(12) United States Patent
Hochi et al.

(10) Patent No.: US 10,668,261 B2
(45) Date of Patent: Jun. 2, 2020

(54) SHEET-LIKE PIECE, SHEET FOR PROMOTING HAIR GROWTH COMPRISING SHEET-LIKE PIECE, AND WHITENING AND WRINKLE AMELIORATING AGENT COMPRISING SHEET-LIKE PIECE

(71) Applicant: QUARRYMEN&Co. Inc., Tokyo (JP)

(72) Inventors: Hiroshi Hochi, Machida (JP); Yasuhiro Yamashita, Tokyo (JP)

(73) Assignee: QUARRYMEN&CO. INC., Tokyo (JP)

( * ) Notice: Subject to any disclaimer, the term of this patent is extended or adjusted under 35 U.S.C. 154(b) by 113 days.

(21) Appl. No.: 15/790,335

(22) Filed: Oct. 23, 2017

(65) Prior Publication Data

US 2018/0071504 A1 Mar. 15, 2018

Related U.S. Application Data

(63) Continuation of application No. PCT/JP2016/062899, filed on Apr. 25, 2016.

(30) Foreign Application Priority Data

Apr. 27, 2015 (JP) ................. 2015-090521
Apr. 13, 2016 (JP) ................. 2016-079985

(51) Int. Cl.
| | | |
|---|---|---|
| *A61M 37/00* | (2006.01) | |
| *A41G 5/00* | (2006.01) | |
| *A61K 8/02* | (2006.01) | |
| *A61K 8/60* | (2006.01) | |
| *A61K 8/98* | (2006.01) | |
| *A61Q 7/00* | (2006.01) | |
| *A61Q 19/02* | (2006.01) | |
| *A61Q 19/08* | (2006.01) | |

(52) U.S. Cl.
CPC ......... *A61M 37/0015* (2013.01); *A41G 5/00* (2013.01); *A41G 5/0033* (2013.01); *A61K 8/0204* (2013.01); *A61K 8/60* (2013.01); *A61K 8/981* (2013.01); *A61Q 7/00* (2013.01); *A61Q 19/02* (2013.01); *A61Q 19/08* (2013.01); *A61M 2037/0023* (2013.01); *A61M 2037/0046* (2013.01); *A61M 2205/0216* (2013.01); *A61M 2210/04* (2013.01)

(58) Field of Classification Search
CPC .......... A61M 37/00; A41G 5/00; A61K 8/02; A61K 8/98; A61Q 7/00; A61Q 19/08; A61Q 19/02
See application file for complete search history.

(56) References Cited

U.S. PATENT DOCUMENTS 6,611,707 B1 * 8/2003 Prausnitz ........... A61B 5/14514
604/21
2003/0135161 A1 7/2003 Fleming et al.
2007/0119468 A1 5/2007 Hochi

FOREIGN PATENT DOCUMENTS

| EP | 2813211 A1 | 12/2014 |
|---|---|---|
| JP | 3484565 B2 | 1/2004 |
| JP | 2005-113300 A | 4/2005 |
| JP | 2005-514179 A | 5/2005 |
| JP | 4009910 B2 | 11/2007 |
| JP | 2012-092464 A | 5/2012 |
| JP | 555831 * | 5/2012 |
| WO | 2013/118877 A1 | 8/2013 |

OTHER PUBLICATIONS

SK-II Official Site / High End Skin Care & Beauty Products (http://www.sk-ii.com/), printed Oct. 5, 2017, including English translation (5 pages). (discussed in the spec).
Learn More About SK-II & The Miracle Ingredient Pitera™ / SK-II (http://wwwsk-ii.com/about-us-miracle.html), printed Oct. 4, 2017, 7 pages.
International Search Report dated Jul. 12, 2016, issued for PCT/JP2016/062899.

* cited by examiner

*Primary Examiner* — Shirley V Gembeh
(74) *Attorney, Agent, or Firm* — Locke Lord LLP

(57) ABSTRACT

The purpose of the present invention is to provide a sheet-like piece comprising; a base sheet comprising an elastic material; a reservoir layer provided on the surface of said base sheet which contains a physiologically active substance and comprises micro needles; a adhesion layer which is formed in a mesh form on said base sheet and; a adhesion assisting layer which is formed on the surface of opposite side of said base sheet to the surface formed said reservoir layer. As a result, the sheet for promoting hair growth which may restore the state of thin hair to a state before thinning, a whitening and wrinkle ameliorating agent having whitening effect and wrinkle improving effect, and sheet-like piece used for these are provided.

7 Claims, 16 Drawing Sheets

Fig. 4 (A)
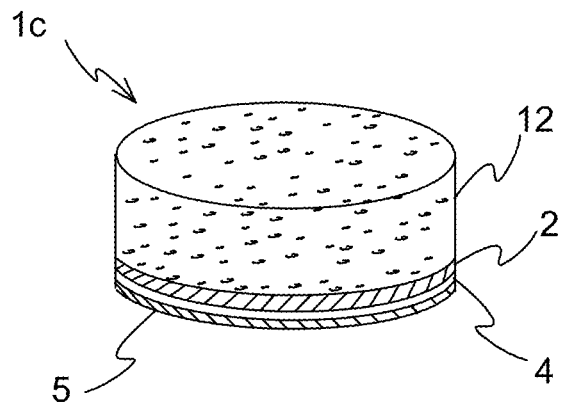
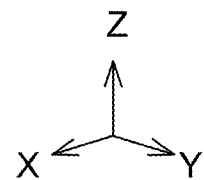
Fig. 4 (B)
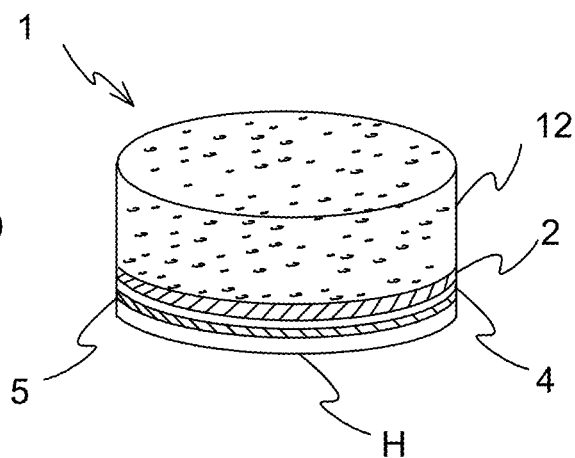
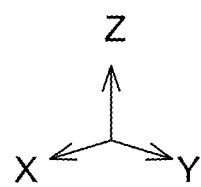

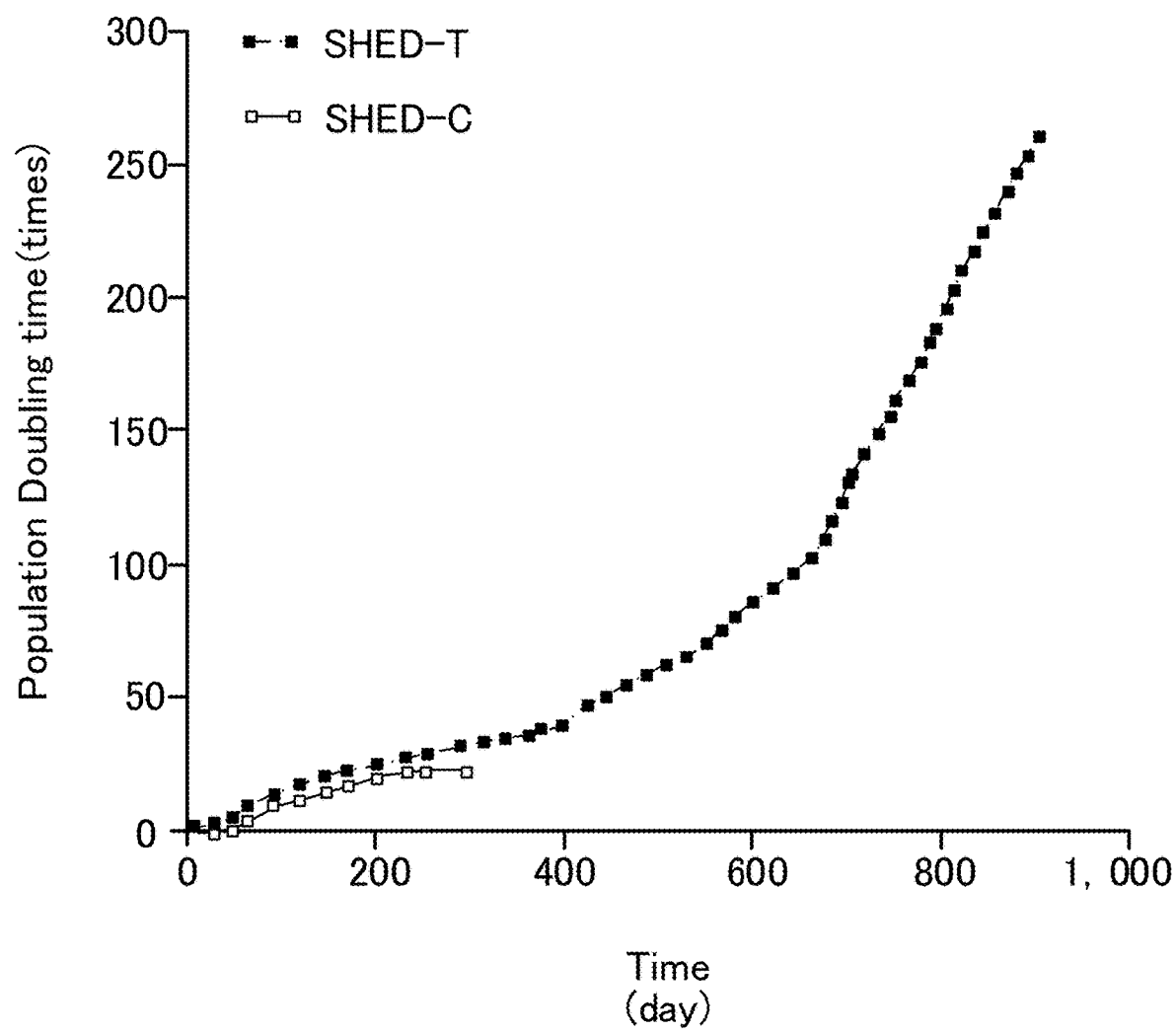

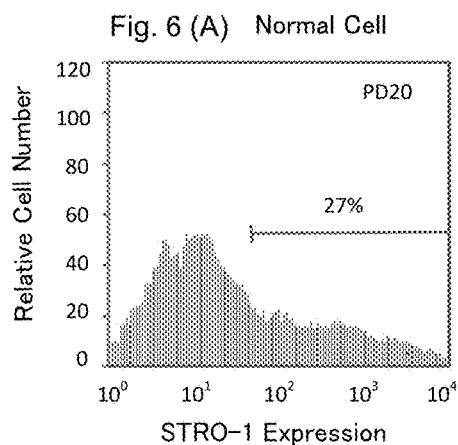
Fig. 6 (A) Normal Cell
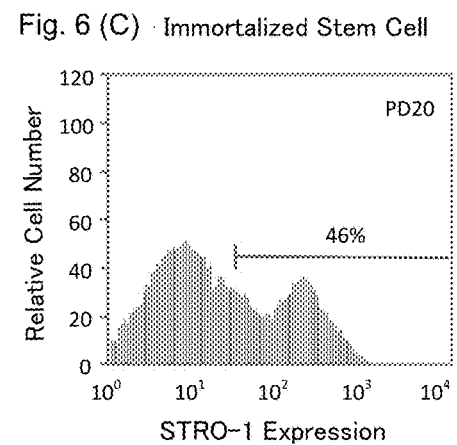
Fig. 6 (C) Immortalized Stem Cell
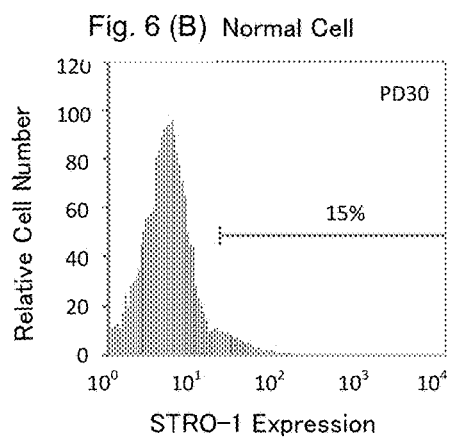
Fig. 6 (B) Normal Cell
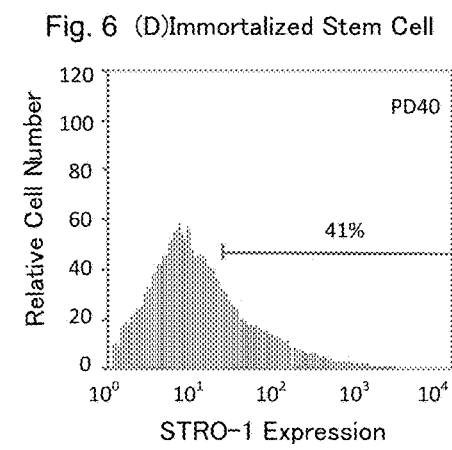
Fig. 6 (D) Immortalized Stem Cell

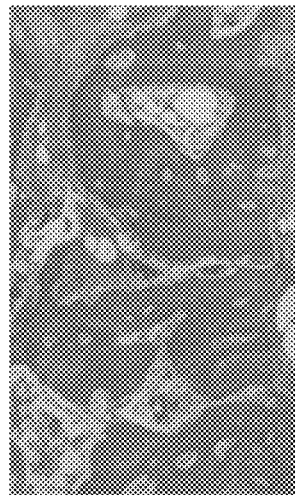
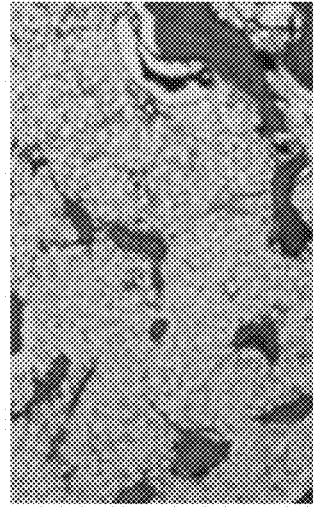
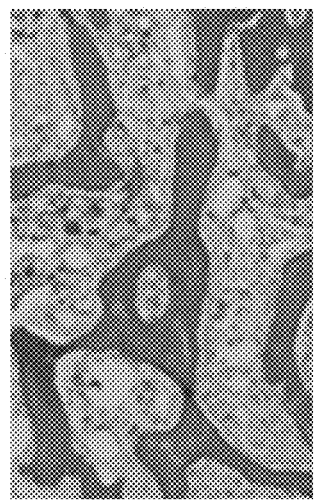
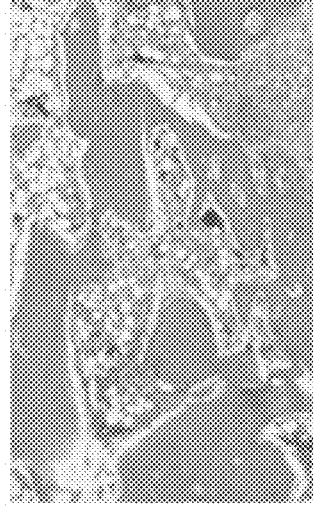
Fig. 7 (A) PD0  Fig. 7 (B) PD10  Fig. 7 (C) PD20
Fig. 7 (D) PD0  Fig. 7 (E) PD10  Fig. 7 (F) PD20
(HE Staining ×200)

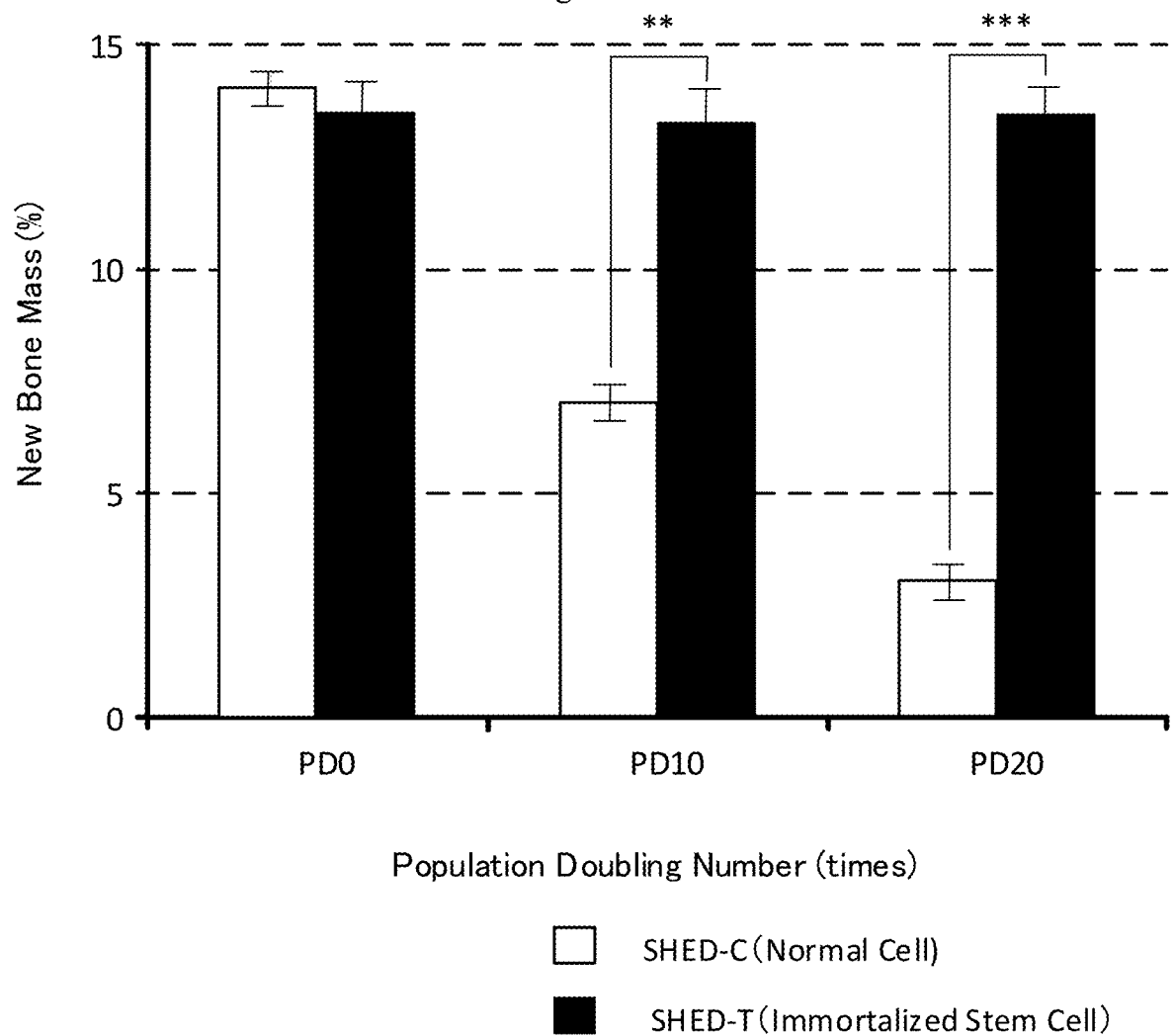

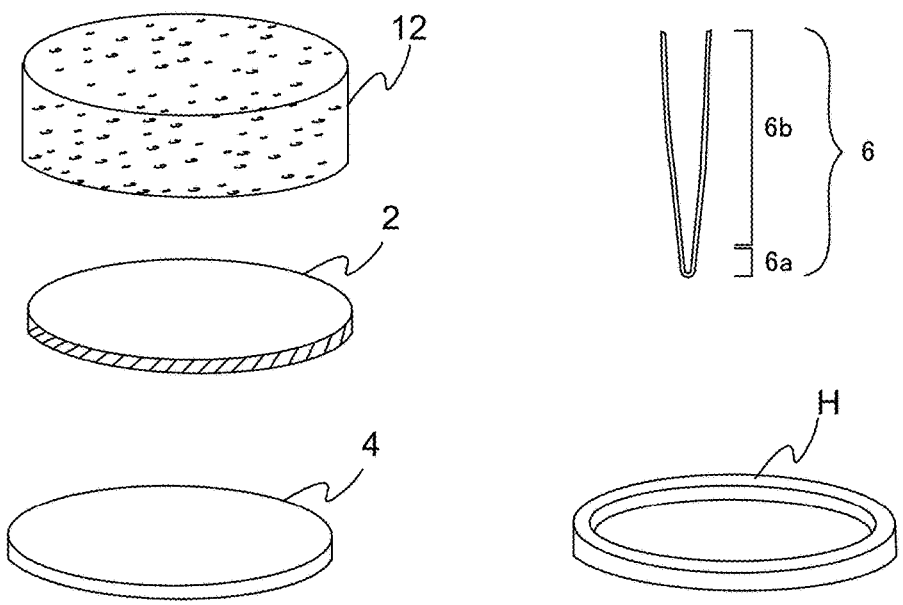
Fig. 11 (A)
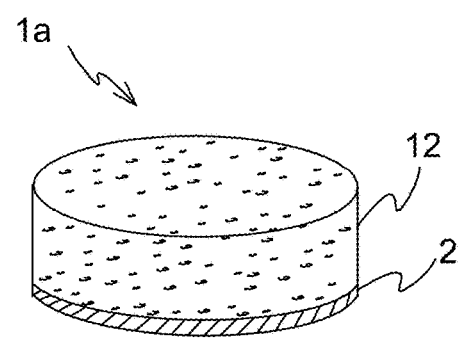
Fig. 11 (B)
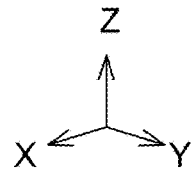

Fig. 14 (A)
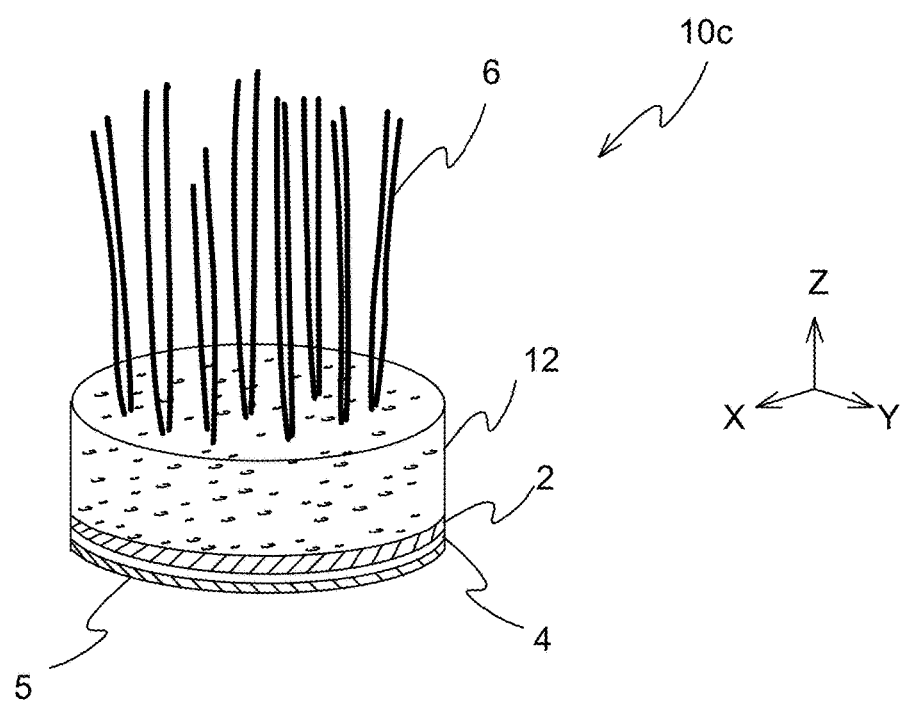
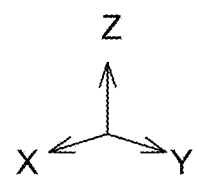
Fig. 14 (B)
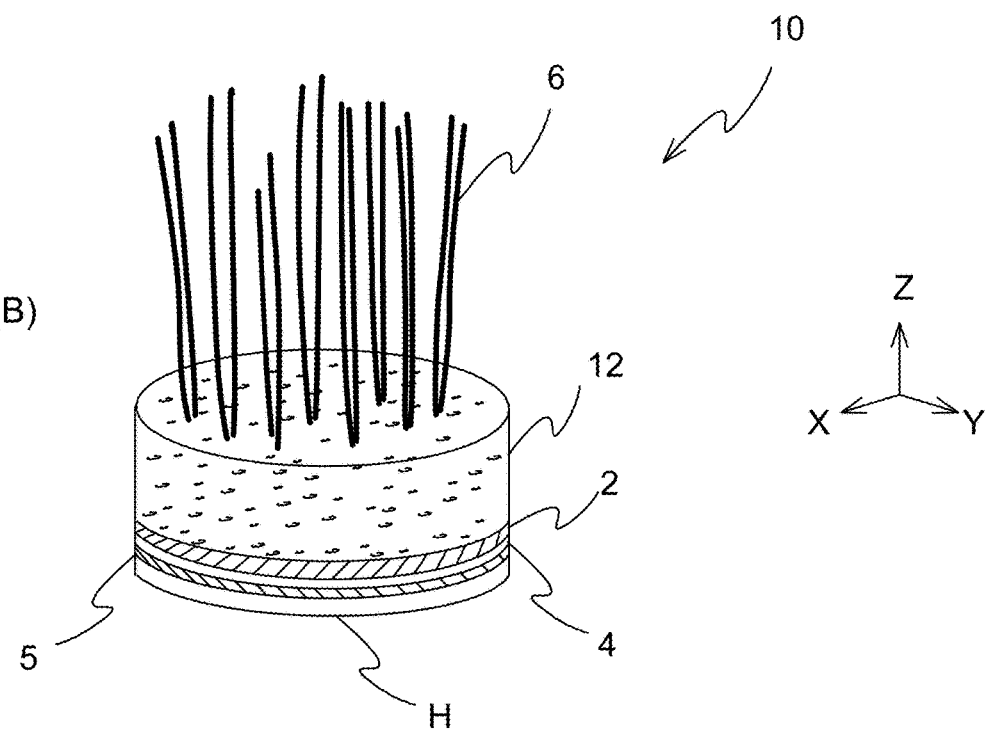
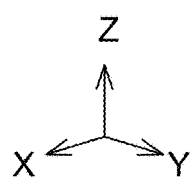

Fig. 15
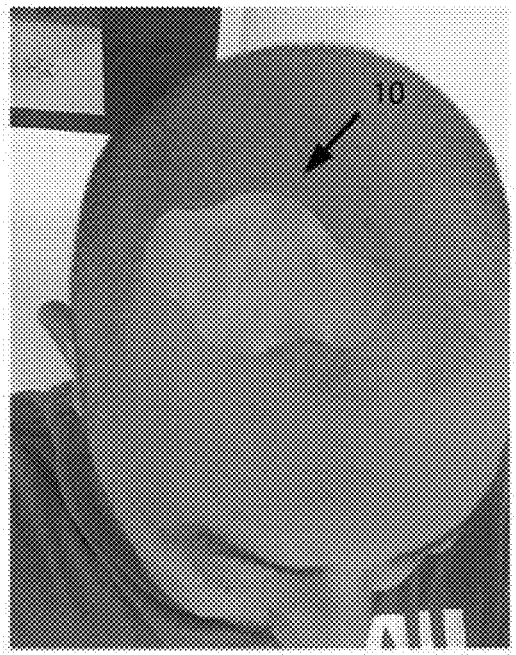
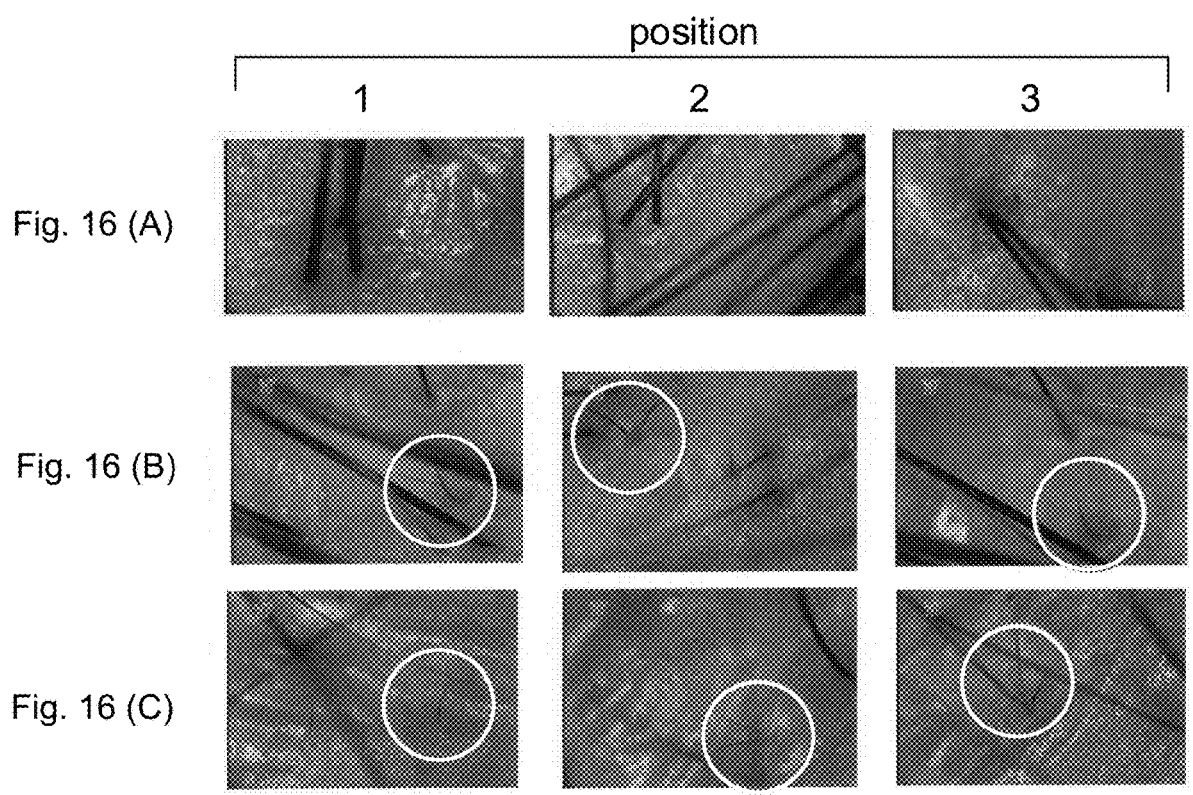

Hair growth effect by growth factor for about 2 months

Hair growth effect by growth factor for about 2 months

Fig. 18 (A)
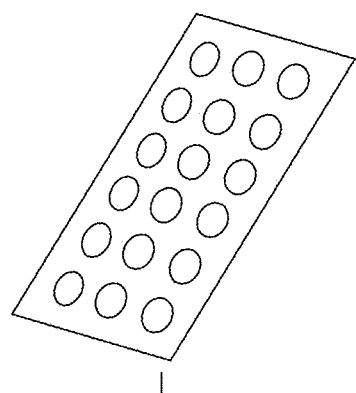
For freckle removal
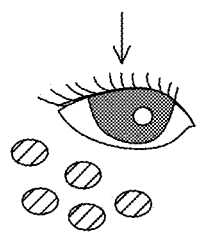
Fig. 18 (B)
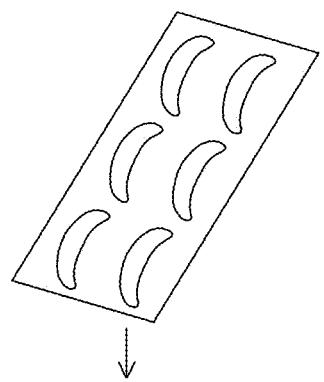
For around eyes
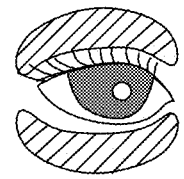
Fig. 18 (C)
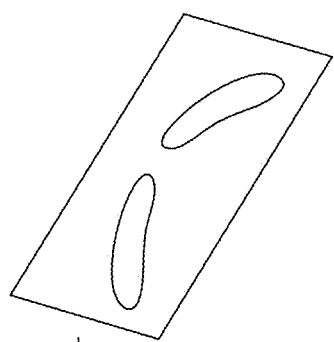
For nasolabial fold
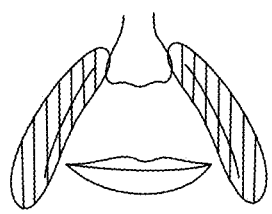
Fig. 18 (D)
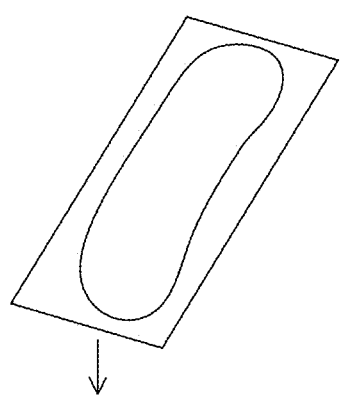
For freckle of forehead

SHEET-LIKE PIECE, SHEET FOR PROMOTING HAIR GROWTH COMPRISING SHEET-LIKE PIECE, AND WHITENING AND WRINKLE AMELIORATING AGENT COMPRISING SHEET-LIKE PIECE

TECHNICAL FIELD

The present invention relates to a sheet-like piece, sheet for promoting hair growth comprising sheet-like piece, and whitening and wrinkle ameliorating agent comprising sheet-like piece. Specifically, it relates to the sheet-like piece for topical absorption of a predetermined physiologically active substance to show the effect thereof, a sheet for promoting hair growth containing the piece, and the whitening and wrinkle ameliorating agent.

BACKGROUND ART

When a person becomes old or falls to a disease, phenomenon such that his/her hair turns gray, gets thin, or losing hair resulting a number of whole hair number decrease happen. Moreover, the person sometimes partially loses the hair due to a variety of diseases including alopecia areata. Also, it is well known that such these cause not only hair aging but also skin aging such as freckle and wrinkle progress. Such skin aging is may developed not only by aging but also other factors such as sunburn and the like.

In particular, the person's hair thins or thins out so that his/her skin of head is shown, when thick hair does not grow at the area from which the hair thins out. Especially, it is conspicuous that the hair is thinning or thins out, when the hair color is dark.

In those cases, since it is very difficult to promote the hair growth having the same thickness as that thinned out, a wig is used. The wig is broadly classified into a reusable type for wearing on the head so as to cover the whole head, and the disposable type comprising a base sheet with flocking materials and adhesion layer for adhering the base sheet on the scalp (hereinafter, it is often referred to as "hairpiece")(see the patent document 1).

It is important that an unnatural feeling in appearance is not given when the disposable type is used. Therefore, the disposable type requires a good fitness on the scalp. Currently, the hairpiece comprising a base sheet composed of a ultra-thin sheet, a flocking material to be flocked in the base sheet and an adhesive layer provided on a back surface of the sheet has been proposed (see the patent document 2, it is referred to as the "prior art 1").

Also, a disposable hairpiece withstanding relatively long-term use is proposed, wherein the adhesiveness of the adhesion layer of the hairpiece is kept relatively low and reusable members and the disposable members being composed of the hairpiece are separable (see the patent document 3, it is referred to as the "prior art 2").

Moreover, the cosmetics containing a variety of components, such as whitening that make freckle inconspicuous, wrinkle ameliorating that ameliorate the wrinkles, and the like, are commercially available (see the non-patent document 1, it is referred to as the "prior art 3").

PRIOR ART

Patent Document

[Patent Document 1] JP 3484565 B2
[Patent Document 2] JP 4009940 B2
[Patent Document 2] JP 2012-92464 A

Non Patent Document

[Non Patent Document 1] http://www.sk-ii.jp/ja/whats-new/skin-solut ions/Four-Steps-To-Reducing-Spots.aspx?utm_source=yahoo&utm_medium=c pc&utm_content=pc_cpc&utm_campaign=skincare

SUMMARY OF THE INVENTION

Problems to be Solved by the Invention

The prior arts 1 and 2 are excellent technology that it makes pretend the thinned hair at present is not changed before hair thinning by using a wig or hairpiece.

However, even if the disposable wig or hair piece proposed in the prior art 1 or 2 are used, the status of the hair stays as is and it is not return to that before hair thinning. Therefore, there is a problem to keep using the wig or the hairpiece continuously so as to match them to the change of the hair.

Note that, in the prior art 2, matters to be improved in the prior art 1 have been partially solved, however, difficulty for fitting the wig or the hairpiece on their scalp by the user himself is still unchanged. That is, the base sheet is ultra-thin, of which thickness is about 30 μm and it indefinitely deforms when the wig or the hairpiece is fit. Therefore, the user substantially could not fit the wig or the hairpiece to his head by himself. By this, the user had to go to a store where they bought the wig or the hairpiece for fitting it by an expert.

However, the user tends to dislike visiting the store, because they are observed by others when the wig or the hairpiece is fitted to their head.

When a person is bold, especially he is prematurely bald; he would like to use the wig or the hairpiece. However, he is embarrassed to go to the store for fitting the wig or the hairpiece so that finally he sometimes gives up to fit it.

As a result, it is known that the person who should become the user behaves passively, or his personality becomes gloomy.

Also, the dark colored hair makes hair thinning conspicuous, and the thinner hair conditions lead that the person is aged. Therefore, there is strong social need for increasing the hair strands to give a young-looking impression. Moreover, there is another strong need from the view point that the increase of the hair strands makes to use the wig or the hairpiece unnecessary, by this it saves the time and cost required for fitting the wig or the hairpiece.

Furthermore, recently, cosmetics showing whitening effect are noticeable and a variety of cosmetics are commercially available (the prior art 3); however, they cause an adverse effect such as vitiligo, and those became big troubles for the user. It is considered that the whitening effect comes from the suppression of melanin synthesis in skin cells so that tyrosinase activity inhibitor and the like are compounded in such cosmetics.

However, there are problems that such whitening or wrinkle ameliorating cosmetics gives unpleasant sensation after the application, and their effect is maintained in a short time. Therefore, the social needs for such cosmetics without such a problem are increasing.

Means for Solving the Problem

The present invention was completed under the situation as described above. Its purpose is to provide a sheet for promoting hair growth to revive them before they became thinner by using the sheet.

That is, the first aspect of the present invention is a sheet-like piece comprising: a base sheet made of an elastic material; a reservoir layer, which contains a physiologically active substance, with plural micro needles extending in opposite direction to said base sheet, being arranged on one side surface of the base sheet; a mesh-formed adhesion layer formed on the opposite side surface of the reservoir layer adhered to the base sheet; and an adhesion assisting layer being detachably arranged on the opposite surface, from which said reservoir layer is formed, of said base sheet, wherein a tip of said micro needle protrudes from said adhesion layer.

Here, it is preferable that said elastic material is composed of a translucent synthetic resin having moisture permeability with less than 0.1 mm of thickness. Also, it is preferable that said reservoir layer comprises a mixture of a water soluble polymer, and either a monosaccharide or a disaccharide, and a mixture of said physiologically active substance.

Also, it is preferable that aid water soluble polymer is at least any one of the polymer selected from the group consisting of collagen, gelatin, hyaluronic acid, dextrin, dextran, proteoglycan, sodium chondroitin sulfate, carboxymethyl cellulose, hydroxyethyl cellulose hyaluronic acid and physiologically acceptable salt thereof. It is preferable that said monosaccharide or said disaccharide is any one selected from the group consisting of glucose, fructose, sucrose, lactose, trehalose and mixture at least two thereof.

Also, it is preferable that said physiologically active substance is contained in a culture supernatant of dental pulp stem cell and said culture supernatant of dental pulp stem cell is lyophilized powder. And, it is preferable that said dental pulp stem cell is an immortalized cell by being introduced a combination of genes, (i) at least one gene selected from the group consisting of bmi-1, HPV-E6 and HPV-E7, and (ii) either one of hTERT or pTERT. Moreover, it is preferable that said dental pulp stem cell is derived from human or swine.

It is preferable that said adhesion layer is formed by silicon based adhesive agent for medical purposes. Furthermore, it is preferable that said adhesion assisting layer is composed of spongy member and said spongy member is composed of any one of material selected from the group consisting of urethane, silicon, pulp paper, styrene, vinyl and cloth.

Also, it is preferable that the sheet-like piece further comprise a frame-shaped supporting member being detachably arranged on the opposite surface of the adhesion layer, on which the reservoir layer is formed on one surface; wherein, said supporting member has higher thickness than the height of the micro needle tip extruding from said adhesion layer.

Here, it is preferable that said supporting member is a sheet-shaped member made of plastic or metal. It is preferable that said sheet-shaped member made of metal is made of aluminum.

Another aspect of the present invention is a sheet for hair growth promotion comprising the sheet-like piece of the present invention. Here, it may further comprise hair prostheses flocked in a predetermined density in said base sheet contained in said sheet-like piece. Here, it is preferable that said hair prostheses is fixed in said base sheet by using UV ray curable resin. Also, it is preferable that bottom surface area of said base sheet is the same size as the surface of a fingertip.

Furthermore, it is preferable that said hair prostheses is penetrated said adhesion assisting layer and is flocked in said base sheet. Here, it is preferable that said hair prostheses penetrates said base sheet and is fixed to said base sheet on the side of reservoir layer of said base sheet.

Also, it is preferred that the sheet for hair growth promotion in the present invention further comprises a frame-shaped supporting member having higher thickness than the height of the micro needle tip extruding from said adhesion layer of said sheet-like piece. It is preferable that such a supporting member is a sheet-shaped member made of plastic or metal. Here, it is preferable that said sheet-shaped member made of metal is made of aluminum The other aspect of the present invention is a whitening and wrinkle ameliorating agent comprising a sheet-like piece of which reservoir layer in said sheet-like piece contains a lyophilized supernatant. It is preferable that it further comprises a supporting member to maintain the sheet-like piece, and that said supporting member is a sheet-shaped member made of plastic or metal. Here, it is preferable that said sheet-shaped member made of metal is made of aluminum.

Advantageous Effect of the Invention

According to the present invention, since the sheet-like piece is optionally cut in size, it is applied to a variety of sites such as scalp, face and others to in an appropriate size to efficiently introduce the physiologically active substances therein.

Also, according to the present invention, the sheet for hair growth promotion is provided for promoting the hair growth by being applied on the area where hair is thinned or almost thinned out. Furthermore, according to the present invention, the whitening and wrinkle ameliorating agent, which has both of whitening effect for lightning the freckle or wrinkle amelioration effect for reducing the wrinkle, may be provided by applying to the freckle part and deep wrinkled part.

BRIEF DESCRIPTION OF DRAWINGS

Fig.2(A) shows a cross-sectional view and Fig 2(B) a shows perspective view.

FIG. 4(A) and FIG. 4(B) are figures (No. 2) for explaining the manufacturing process of the sheet-like piece in FIG. 1(A) and FIG. 1(B).

FIG. 5 is a graph showing time dependent change of population doubling time for an immortalized stem cell, which produces culture supernatant to be used for producing the sheet for hair growth promotion in present invention.

FIG. 6(A), FIG. 6(B), FIG. 6(C) and FIG. 6(D) are graphs for confirming whether the STRO-1 expression of said immortalized stem cell decreases or not, depending on the increase of population doubling time (PD).

FIG. 7(A), FIG. 7(B), FIG. 7(C), FIG. 7(D), FIG. 7(E), and FIG. 7(F) show an eosin-hematoxylin staining for confirming whether osteogenesis ability of said immortalized stem cell decreases or not, depending on the increase of population doubling time (PD).

FIG. 8 is the graph showing the change for the population doubling time of said immortalized stem cell and osteogenic productivity for neonatal bone.

FIG. 11(A) and FIG. 11(B) are schematic diagrams (No. 1) for explaining the manufacturing process of the sheet-like piece in FIG. 9.

FIG. 14(A) and FIG. 14(B) are figures(No. 3) for explaining the manufacturing process of the sheet-like piece in FIG. 9.

FIG. 15 is a photograph showing the sheet for hair growth promotion of the invention is applied to scalp.

FIG. 16(A), FIG. 16(B) and FIG. 16(C) show enlarged photographs, Fig. 16(A) shows the scalp state before applying the sheet for hair growth promotion of the invention, Fig 16(B) shows the state of that 3 days after fitting it, and Fig. 16(C) shows the hair growing state 7 days after fitting it.

Fig. 17(A) shows the change in a parietal region after the application, and Fig. 17(B) shows the change of the area from which hair was fallen by alopecia areata behind the ear after the application.

FIG. 18(A), FIG. 18(B), FIG. 18(C) and FIG. 18(D) are schematic diagrams showing a variation of the shapes for the whitening and wrinkle ameliorating agent of the present invention. In the figure, Fig. 18(A) is that for removing freckle, Fig 18(B) is that for ameliorating the wrinkle around eyes, Fig. 18(C) is that for ameliorating nasolabial folds, and Fig. 18(D) is that for wrinkle on forehead.

MODE FOR CARRYING OUT THE INVENTION

The present invention is explained in detail below. Note that, in the following explanation or figure, the same or equivalent element is denoted by the same symbol, and duplicate explanation is omitted.

Figure 1:
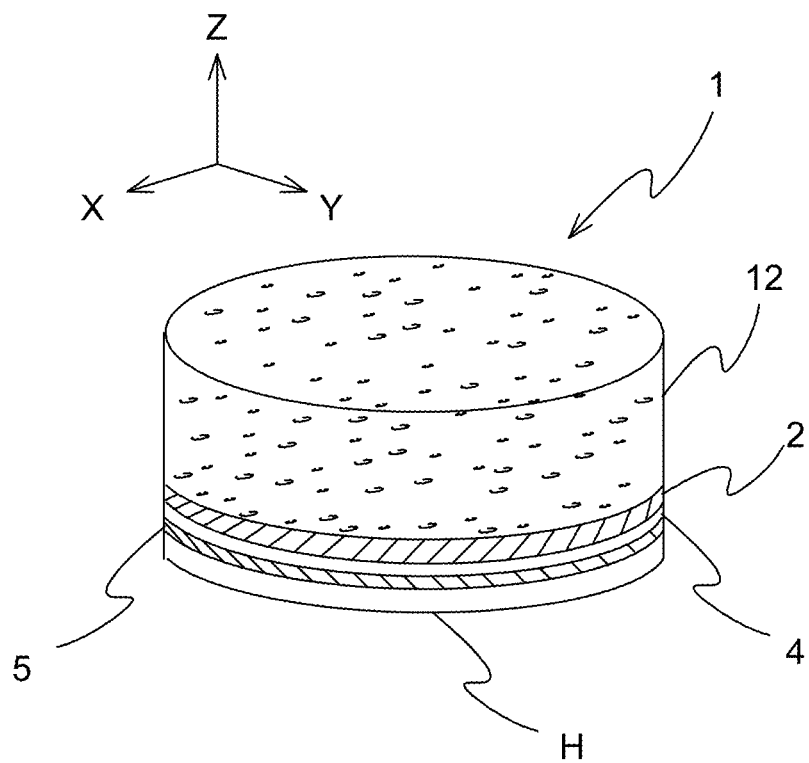
FIG. 1(A) and FIG. 1(B) are pattern diagrams showing the structure of the sheet-like piece of the present invention.
Figure 1:
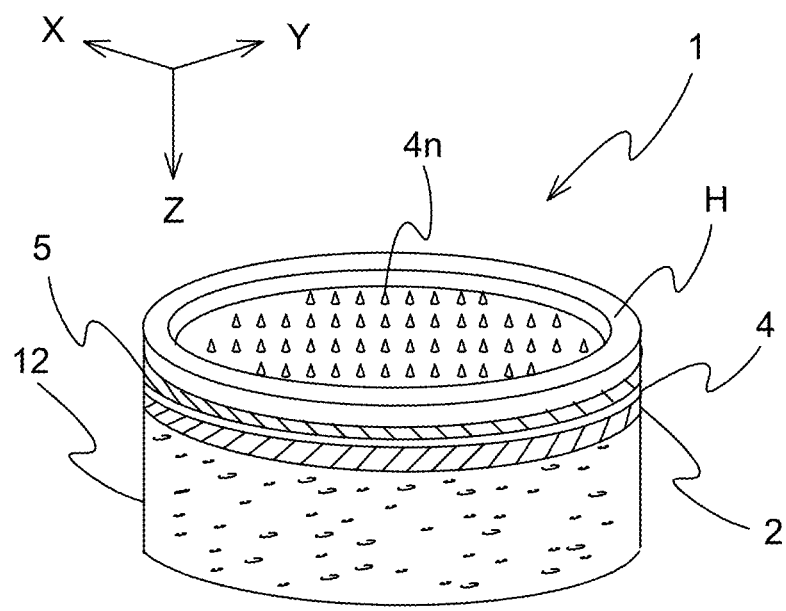

As shown in FIG. 1, the sheet-like piece 1 of the present invention comprises, (a) a base sheet 2 made of an elastic material; (b) a reservoir layer 4 put on the surface of one side (−Z direction) of the base sheet 2 which contains a physiologically active substance and is formed plural micro needles 4n extending in opposite direction (−Z direction) to said base sheet; (c) a adhesion layer 5 which is formed in a mesh-formed on the opposite surface of the side (−Z direction) of the base sheet 4; (d) adhesion assisting layer 12 which is formed to be detachably arranged on the opposite surface of the side (+Z direction) of the base sheet 2 to the surface formed the reservoir layer. Here, tip of the micro needles 4n protrude from the adhesion layer 5.

Also, the sheet-like piece 1 further comprises (e) frame-shaped supporting member H which is detachably arranged on the opposite surface of side (−Z direction) of the adhesion layer 5 to the surface formed the reservoir layer 4. Here, the supporting member H has higher thickness than the height of the tip of micro needle 4n extruding from the adhesion layer 5.

Note that, plural sheet-like piece 1 is placed on a metallic plate member or a plastic plate member. Here, the side surface in −Z direction of the supporting member H of sheet-like piece 1 is strongly adhered to the plate member by adhesive agent. Thus, the sheet-like piece 1 placed on the plate member may be separated from the plate member in a state that the supporting member is left on the plate member. It is preferable from the viewpoint of weight and cost that the supporting member H is made of a plastic or metal sheet-shaped member comprising circular member of which form conform to the sheet-like piece 1 in order to protect the micro needles 4n formed on the sheet-like piece 1. It is preferable from the viewpoint of easy processing that said supporting member is made of aluminum when it is made of metal.

It is preferable that the elastic material constituting the base sheet 2 has three features of moisture permeability, the thickness of less than 0.1 mm and translucent synthetic resin. This is due to the following three reasons.

Firstly, if the elastic material lacks moisture permeability, since moisture contained in sweat does not evaporate, the area on which the material is placed get sweaty. It is not only unpleasant but also sometimes has adverse effects to the skin. Secondly, if the thickness of the material is 0.1 mm or more, it is impossible to naturally fit along the skin. For example, when the sheet for hair growth promotion is fit on the scalp or the whitening and wrinkle ameliorating agent is applied onto the skin, unnatural appearance confirmed by sight remains and it suggests that the sheet is fitted. Thirdly, when the elastic material is translucent, it makes the sheet applied on any sites on the skin inconspicuous.

As such elastic materials there are mentioned, for example, polyurethane resin, silicone resin, a nylon resin and the like. Among them, a silicone material may be preferably used. The translucent synthetic resin having vapor permeability with the thickness of about 20 to 60 μm has excellent fitting property to the skin, and also the fitted material is almost invisible. Note that, when such a material is employed in the whitening and wrinkle ameliorating agent of the invention and the agent is fitted on the face, the person may make up on it.

Figure 2:
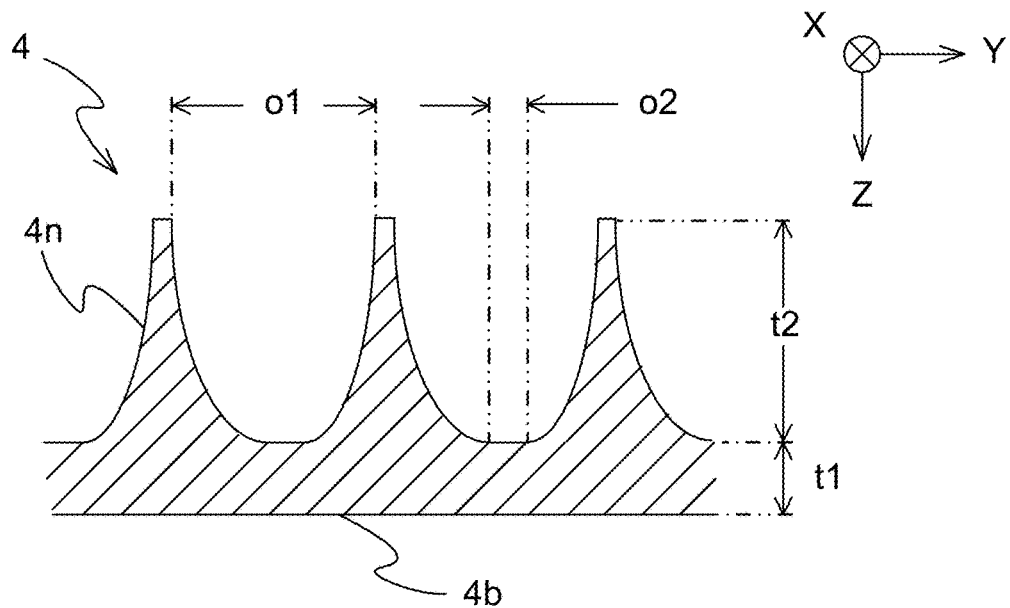
FIG. 2(A) and FIG. 2(B) are schematic diagrams showing the form of micro needles.
Figure 2:
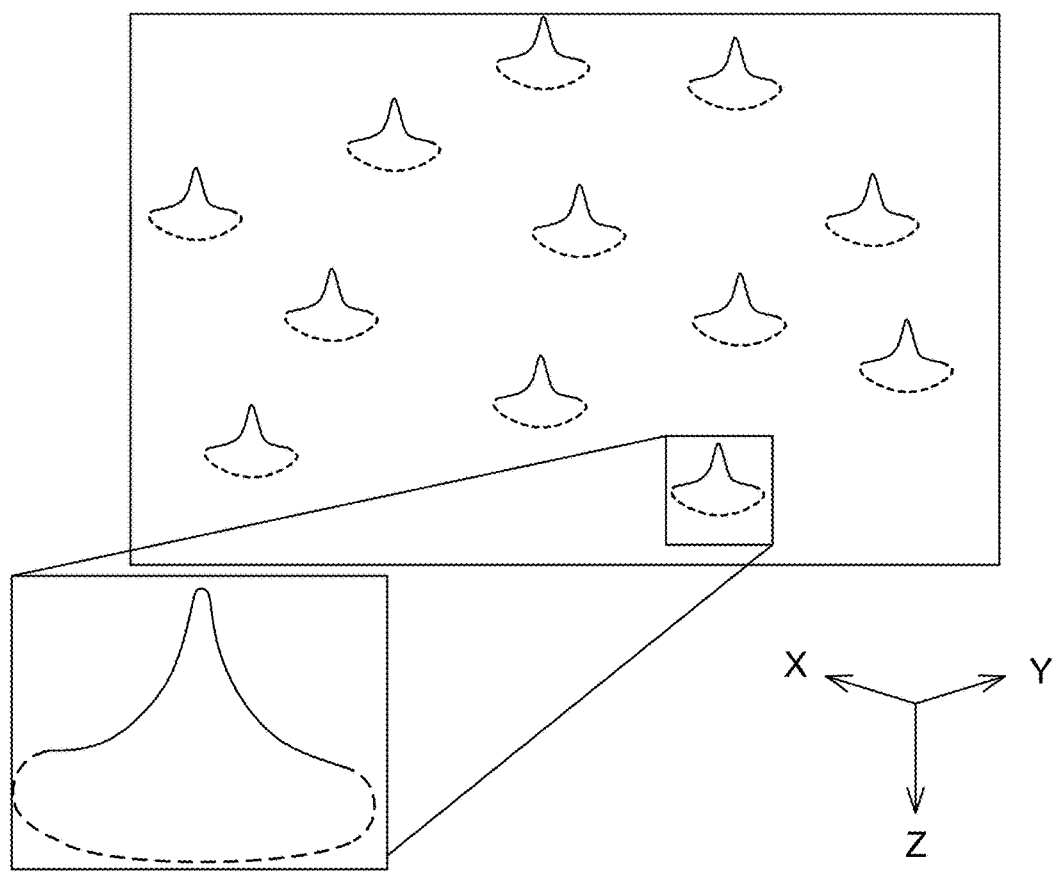

As shown in FIG. 2, plural micro needles 4n extending in −Z direction are formed on the reservoir layer 4. It is preferable that the concave portions for forming the micro needles 4n has a conical shape which has upper diameter of of about 0.1 to 0.3 mm, bottom diameter o2 of about 0.03 to 0.05 mm and depth 2 of about 0.6 to 1.0 mm. Also they are arranged in a lattice pattern. It is preferable that the concave portion is about 50 to 100 pieces/cm².

It is preferable that the reservoir layer 4 contains the mixture of a water soluble polymer, and either of monosaccharide or disaccharide, and the mixture of said physiologically active substances. It is preferable that the water soluble polymer is at least any one selected from the group consisting of collagen, gelatin, hyaluronic acid, dextrin, dextran, proteoglycan, sodium chondroitin sulfate, carboxymethyl cellulose, hydroxyethyl cellulose hyaluronic acid, and physiologically acceptable salt thereof.

The micro needles 4n having appropriate sizes are formed by containing these components. These microneedles 4n formed lead to introduce the physiologically active substance described later efficiently into the skin. Among them, hyaluronic acid is preferable used. Also, as the monosaccharide or disaccharide, any one of sugar selected from the group consisting of glucose, fructose, sucrose, lactose, trehalose and mixture at least two thereof. Glucose is preferably used because of cost and low irritation.

It is preferable that the content of the monosaccharide or disaccharide in the composition in the composition composed of the water soluble polymer and either of the monosaccharide or disaccharide is 0.2 to 4 wt %, because of dissolution time of micro needles 4n in the skin and mechanical strength thereof. Since the dissolution time become too short such as not longer than 30 minute, when the content of the monosaccharide or disaccharide exceeds 5%. Therefore, their content is preferably 0.2 to 4 wt %.

Also, the adhesion layer 5 is preferably formed by using a silicon type adhesive agent for medical purposes; because it does not cause troubles such as rash after applying the sheet or skin turns red after peeling off it. Furthermore, it is preferable that the micro needles 4n protrude from the mesh formed by the adhesion layer 5 in the appropriate size, because it enables to introduce the physiologically active substances efficiently into the skin.

Also, the adhesion assisting layer is preferably composed of spongy member. It is preferably selected from the group consisting of urethane, silicon, pulp paper, styrene, vinyl and cloth.

Figure 3:
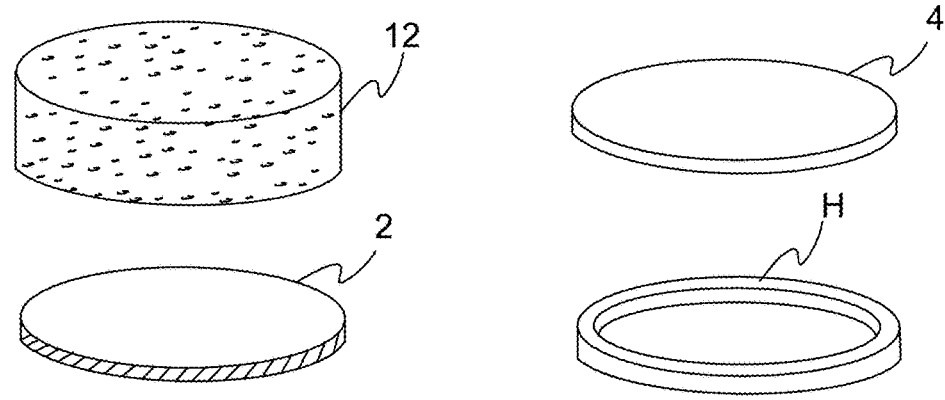
FIG. 3(A), FIG. 3(B) and FIG. 3(C) are figures (No. 1) for explaining the manufacturing process of the sheet-like piece in FIG. 1(A) and FIG. 1(B).
Figure 3:
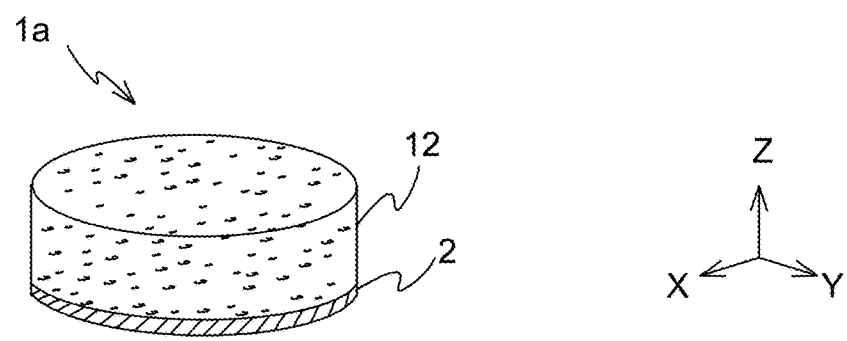
Figure 3:
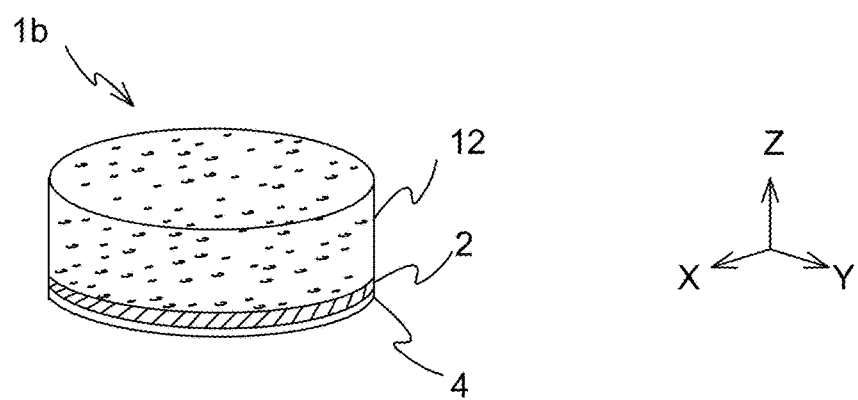

The sheet-like piece 1 described above is produced as follows. At first, the base sheet 2, the reservoir layer 4, the adhesion assisting layer 12, the supporting member H and a variety of adhesive agents are prepared as shown in FIG. 3(A).

Next, the adhesion assisting layer 12 is adhered detachably on the +Z direction side surface of the base sheet 2 by using one adhesive agent to form the laminated body 1a as shown in FIG. 3(B). By this, it is preferable to arrange the adhesion assisting layer 12, because it enables for efficient proceeding of subsequent formation of the reservoir layer 4 and the like.

Next, the reservoir layer 4 is firmly adhered to the −Z direction side surface of the base sheet 2 by using another adhesive agent to form the laminate body 1b shown in FIG. 3(C). Subsequently, the adhesion layer 5 is formed by applying a pressure sensitive adhesive in a mesh form onto the area without the micro needles 4n to form the laminate body 1c shown in FIG. 4(A).

Next, after cutting the laminate body 1c to the desired size, the supporting member H is adhered on the −Z direction side surface of the adhesion layer 5. As a result, a sheet-shaped piece 1 is produced as shown in FIG. 4 (B).

Thus produced sheet-shaped piece 1 is placed on a ring-shaped sheet holder made of the metallic plate member having both desired thickness and size or the plastic plate member to be a final product.

Note that, the physiologically active substance included in reservoir layer 4 is obtained as follows.

Firstly, a dental pulp stem cell used for producing the culture supernatant which contains the physiologically active substance is prepared. Such stem cell is introduced the combination of (i) at least one gene selected from the group consisting of bmi-1, HPV-6 and HPV-E7, and (ii) any gene hTERT or pTERT. This is because that the dental pulp stem cell may be passage more than 100 times by introducing the combination of these genes.

Firstly, a mammal dental pulp cell is isolated as follows when the dental pulp stem cell described above is prepared. Here, "dental pulp cell", is one of stem cells included in the nerve for the teeth, and has the regeneration ability. Since it is protected by hard material, teeth, does not permeate UV light or radioactive ray, the genes in them is not easily damaged.

Among the genes described above, hTERT is a gene coded for human telomere repair enzyme, and pTERT is a gene coded for porcine telomere repair enzyme respectively. The gene, bmi-1 produced one of proteins being composed of polycomb group complex, Bmi-1. Bmi-1 is necessary for maintaining the hematopoietic stem cells and may increase the hematopoietic stem cell by enhancing the activity. Also, HPV-E6 and E7 are the early genes of HPV-16 or HPV-18 existing in the open reading frame encoding the early gene used for the auto-reproduction by human papilloma virus.

In the following, it is explained as an example for the preparation of immortalized cell by using the dental pulp obtained from the human exfoliated deciduous teeth.

Firstly, the exfoliated dens deciduous are disinfected by using, for example, chlorhexidine, and a crown of the tooth is divided in horizontal direction by using a dental reamer to recover the dental pulp. Next, the obtained dental pulp tissue is suspended in the basal media, for example, such as Dulbecco's modified eagle's MEM (Dulbecco's Modified Eagle's Medium, herein below, it is referred to as "DMEM") containing 5 to 15% (v/v) of calf serum (calf serum, herein below, it is sometimes referred to as "CS"), and 50 to 150 U/mL of antibiotics, and the like.

Then, they are treated by using 1 to 5 mg/mL of collagenase and 1 to 5 mg/mL of dispase at 37° C. for 0.5 to 2 hrs. After enzyme treatment, centrifugation operation is performed for 3 to 10 minutes (3,000 to 7,000 rpm) to recover the dental pulp cell. Depending on the necessity, the cells are selected by using a cell strainer. The selected cells are, for example, resuspended in 3 to 6 mL of the basal medium to plate in a dish having 4 to 8 cm of diameter for adherent cell culture.

Subsequently, the medium, for example, DMEM containing 10% FCS is added, and then the cells are incubated in 5% $CO_2$ incubator at 37° C. for about 2 weeks. After removal of the medium, the cells are washed from 1 to several times with PBS and the like. Instead of the removal of the medium and wash of the cells, the adherent dental stem cells which formed colonies may be collected. The adherent dental pulp stem cells are treated by using a solution including both of 0.025 to 0.1% trypsin and 0.3 to 1 mM EDTA for several minutes at 37° C. to be detached from the dish. Next, detached cells are collected.

After the enzyme treatment, the sample is centrifuged for about 3 to 10 minutes (3,000 to 7,000 rpm) to collect the dental pulp cell. Depending on the necessity, the cells are separated by using a cell strainer. The separated cell is, for example, resuspended in 3 to 6 mL of the basal medium to be plated into the dish for adherent cell culture having 4 to 8 cm diameter.

Next, the culture medium, for example, DMEM supplemented with 10% FCS is added; then, they are incubated in a 5% incubator at 37° C. for about 2 weeks. The culture supernatant is removed, and the cells are washed with PBS in 1 to several times. Instead of removing of the culture medium and washing of the cells, the adherent dental pulp cells forming colonies may be collected. The adherent dental pulp stem cells are detached from the dish, for example, by using 0.025 to 0.1% of trypsin and 0.3 to 1 mM of EDTA for several minutes at 37° C., and then they are collected.

Subsequently, the selected adherent cells obtained as mentioned above are cultured. For example, the dental pulp stem cells obtained as mentioned above are plated to the dishes for the adherent cell culture, and then cultured under the conditions of 5% $CO_2$ and at 37° C. in the incubator. By this, primary cultured cells (SHED-P) of human exfoliated dens deciduous stem cells may be obtained.

In passage culture, for example, the cells are collected by using trypsin and EDTA, when the cells become sub-confluent or confluent with macroscopic observation as mentioned above. Then, the cells are plated again in the culture dish including the culture medium.

Here, the term, "sub-confluent", means the situation that the cells adhere about 70% of the bottom area of the culture vessel. For example, the passage is performed 1 to 8 times, and selected cells are propagated up to the necessary cell number, for example, about $1\times10^7$ cells/mL. After culturing as described above, the cells are collected to store in liquid nitrogen. The cells collected from a variety of donor may be stored in the form of dental pulp stem cell bank.

The combination of (i) at least one gene selected from the group of bmi-1, HPV-E6 and HPV-E7 and (ii) any gene of hTERT or pTERT may be introduced as follows. Firstly, a plasmid for insertion of the combination of the genes is prepared, and then it is inserted into a shuttle vector, for example, pShuttle2 to clone the genes. After that, E. coli is transformed by using the pShuttle2 to select kanamycin resistant transformant (hereinafter, it is referred to as Kn+) by using kanamycin as a marker. The DNA of the Kn+ is purified to identify a recombinant by analyzing restriction sites.

Next, for example, PI-Sce I and I-Cue I are used to cut out an expression cassette from the shuttle vector, and then it is ligated into adenovirus vector, for example to obtain the Adeno-X viral DNA. The obtained ligation product is cleaved by using, for example, Swa I, and E. coli is transformed by the cutting product to obtain the transformants.

Among the obtained transformants, for example, ampicillin resistant transformants (hereinafter, it is referred to as Amp+) were selected by using ampicillin and purified to identify a recombinant by analyzing restriction sites. Next, the adenovirus is digested by using Pac I to transfect HEK 293 cells. The recombinant adenovirus is propagated and collected to measure their titers. The virus is purified according to a conventional method; it is used to infect the target cell, SHED-P.

Cell population infected with the virus is stained by using FITC according to the conventional method, and then STRO-1 positive cells are detected by using a flow cytometer. Here, STRO-1 is considered as one of markers for the mesenchymal stem cell having pluripotency in the bone marrow, and it becomes an index for cell immortalization. According to the above-mentioned procedure, the immortalized stem cell from the dental pulp may be obtained.

Next, the obtained immortalized stem cell is cultured in the basal medium, for example, DMEM supplemented with 10% FBS under the condition of 5% $CO_2$ at 37° C. for 24 to 48 hours to obtain the culture sup. In order to collect the culture sup, for example, a Komagome type pipette and the like may be used.

Also, the immortalized stem cell secretes at least two growth factors selected from the group consisting of insulin-like growth factor (IGF), vascular endothelial growth factor (VEGF), transforming growth factor (TGF), and hepatocyte growth factor (HGF) into the culture supernatant. Here, the term "growth factor" is a general term of polypeptides which promote the cell division, bring the morphological change or cell hypertrophy. The growth factors are different depending on the cells which produce them, and they are roughly classified into epidermal growth factor (EGF), fibroblast growth factor (FGF), nerve growth factor (NGF), tumor growth factor (TGF) and the like.

Furthermore, since the receptors on the cell membrane of each cell have tyrosine kinase activity, they phosphorylate tyrosine residues of the proteins by binding of the growth factors to cause the cell growth or proliferation. It is known that there are several examples that the growth factor becomes a mesoderm inducer in the ontogenesis. Also, it is known that there are several examples that the lymphokine becomes the mesoderm inducer in the ontogenesis. Such growth factors may be determined by using the known ELISA, microarray assay and the like.

IGF-1 is the polypeptide having highly similar sequence to insulin, and it causes reactions such as mitogenesis and the like in the culture cells. It is also known that IGF affects the nerve cell growth. VEGF is a glycoprotein family involving to vascurogenesis, which newly forms blood vessels in the area wherein the blood vessels are not yet formed in embryonic stage period of embryogenesis, and angiogenesis, which newly forms the blood vessels by branching and extending from already exists the blood vessels.

TGF-β also becomes a potent growth inhibitor against the variety of the cells, and tightly involves to the cell differentiation, migration and adhesion, and it plays an important role in a broad region such as ontogenesis, tissue reconstruction, wound healing, inflammation and immunity, cancer invasion and metastasis, and the like. Furthermore, HGF has a variety of physiological activity being involved in the regeneration and protection of the tissue and the organ such as the promotion of the cell proliferation and cell motion, anti-apoptosis (cell death), morphogenetic induction, angiogenesis and others to the various cells including hepatocyte.

Each stem cell mentioned above is cultured, for example, in DMEM supplemented with 15% FCS at 37° C. for the predetermined term, thereby the culture supernatant including the growth factors as mentioned above may be obtained. Note that, the culture supernatant of the stem cell includes about 70 kinds of proteins besides IGF-1, VEGF, TGF-0, and HGF.

15 mL of the culture sup from the obtained culture sup is poured into Amicon Ultra Centrifugal Filter Units-10K (Millipore Limited). Then, it is centrifuged with 4,000×g for about 60 minutes to condense about 200 μL. Next, the same volume of PBS as that of culture supernatant is added into the tube, and centrifuged again with 4,000×g for about 60 minutes to replace the solvent to PBS. The obtained 200 μL of the solution is collected into the micro test tube to obtain the condensed stem cell culture supernatant.

Instead of the method by using Amicon as described above, the concentration may be performed by using ethanol precipitation method. For example, 45 mL of 100% ethanol is added to 5 mL of the culture supernatant to mix them and then stood at −20° C. for 60 minutes. After that, it is centrifuged with 15,000×g for 15 minutes at 4° C. to remove supernatant.

Next, for example, 10 mL of 90% ethanol is added to mix well, and then again centrifuged with 15,000×g for 5 minutes at 4° C. After removing the supernatant, the obtained palette may be dissolved in, for example, 500 μL of the sterilized water. After the dissolution, the entire of the volume is collected in the micro test tube, and the condensed stem cell culture supernatant is obtained.

The culture sup obtained as mentioned above may be also lyophilized according to the conventional method to have the pharmaceutical preparation to be prepared at time of use. The obtained preparation may be used for forming the reservoir layer 4 used in sheet-shaped piece 1 of the present invention.

Concretely, the reservoir layer forming material is prepared by mixing the above mentioned water soluble polymer, and either of monosaccharide or disaccharide at the predetermined ratio, and then mixed with the lyophilized culture supernatant powder. For example, about 0.2 to 4 wt % of glucose or dextran is mixed with the water soluble polymer such as hyaluronic acid, polyvinyl alcohol and the like, and a desired amount of the lyophilized culture supernatant is added to be mixed to prepare the reservoir layer forming material.

Then, the sheet is made of the photosensitive resin, and then the micro needles pattern having a shape shown in FIG. 2 (A) is produced by using photolithography. After that, the pattern is printed by electroforming to produce a mold for forming micro needles. It is preferable that the mold has one side of about 8 to 20 cm from the viewpoint of work efficiency. Also, it is preferable that the concave portion for forming the micro needles $4n$ has a conical shape which has upper diameter of of about 0.1 to 0.3 mm, bottom diameter o2 of about 0.03 to 0.05 mm and depth 2 of about 0.6 to 1.0 mm, and are arranged in a lattice pattern. It is preferable that the concave portion is about 50 to 100 recess/cm$^2$ (see FIG. 2 (B)).

Aqueous solution containing about 5 to 20% of solid content is prepared by adding water to the reservoir layer forming material, and poured into the mold at room temperature; then it is subjected to evaporate to dry. After that, in order to obtain the reservoir layer 4 with the micro needle $4n$, the mold is peeled off.

Note that, the sheet-shaped piece 1 produced by the above may be used as an embodiment of the sheet for hair growth promotion or the whitening and wrinkle ameliorating agent by adjusting the amount of physiologically active substances contained. Therefore, the sheet-shaped piece 1 is also described sometimes as the "hair growth promotion sheet 1" or the "whitening and wrinkle ameliorating agent" in the following explanation.

Figure 9:
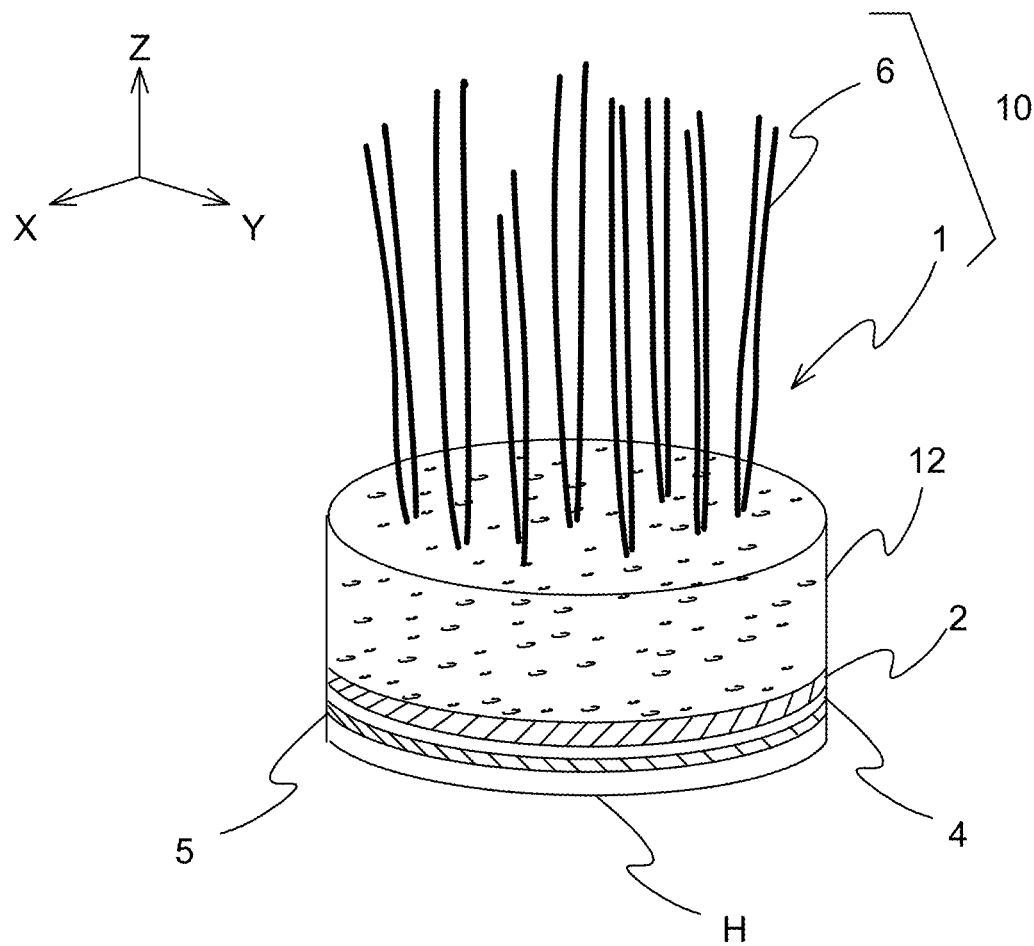
FIG. 9 is the schematic diagram showing the structure of the sheet for hair growth promotion, which also functions as the hairpiece.

Next, another embodiment of the sheet for hair growth promotion is explained. The structure of the hair growth promotion sheet 10, another embodiment thereof, is shown in FIG. 9. As shown in FIG. 9, the sheet for hair growth promotion 10 comprises the sheet-shaped piece 1 and the prostheses 6.

Figure 10:
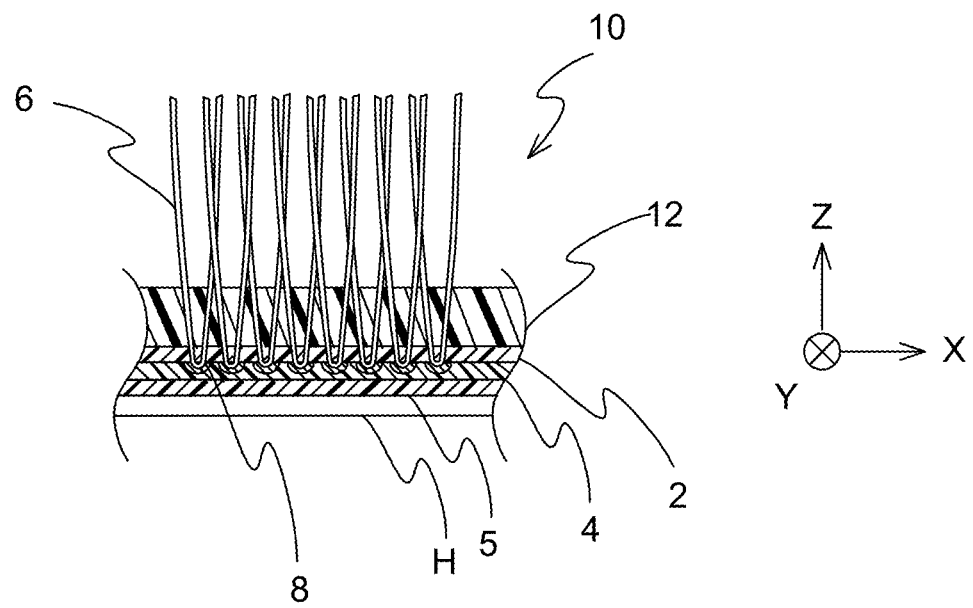
FIG. 10 is a cross-sectional view of the sheet for hair growth promotion in FIG. 9.

As shown in FIG. 10, the prostheses 6 are flocked in the base sheet 2 at a predetermined density. As shown in the FIG. 10, the prostheses 6 penetrates both of the base sheet 2 and the adhesion assisting layer 12, and is fixed in the base sheet 2 on the −Z direction side surface of the base sheet 2.

Since it is premised that the hair growth promotion sheet 10 is used for adhering to the scalp as a whole thereof, skin base is preferably used. Also, the thickness of the hair growth promoting sheet 10 is preferably 20 to 60 µm, because the balance between good adhesion and robustness at attachment and detachment is excellent, and more preferably 30 to 40 µm.

Here, the predetermined density is determined depending on the hair growth conditions of the site on which the hair growth promotion sheet 10 is applied. In general, it is said that Japanese total hair number is about 100,000, and the scalp hair density, numbers of hair in 1 cm$^2$, is 133 to 249 of which average is 199 at sincipit, 114 to 250 of which average is 183 at the forehead, 137 to 235 of which average is 172 at occipit, and 106 to 217 of which average is 130 at the temporal. It may be selected appropriately refer to the figures.

Also, as the prostheses 6, generally used fibers for producing the wig or the hairpiece such as polyester fiber, vinyl chloride fiber, acrylic fiber, flame retardant polyester fiber and the like may be used. Polyester fiber is preferably used because of the cost.

Also, the prostheses 6 are preferably fixed on the base sheet 2 by using UV curable resin, thereby, the prostheses are efficiently fixed on the sheet, preventing from falling out.

The sheet for hair growth promotion 10 described above is produced as follows. Firstly, as shown in FIG. 11(A), the base sheet 2, the reservoir layer 4, the adhesion assisting layer 12, the supporting member H, plural hair prostheses 6 and a variety of adhesive agents are prepared.

Figure 12:
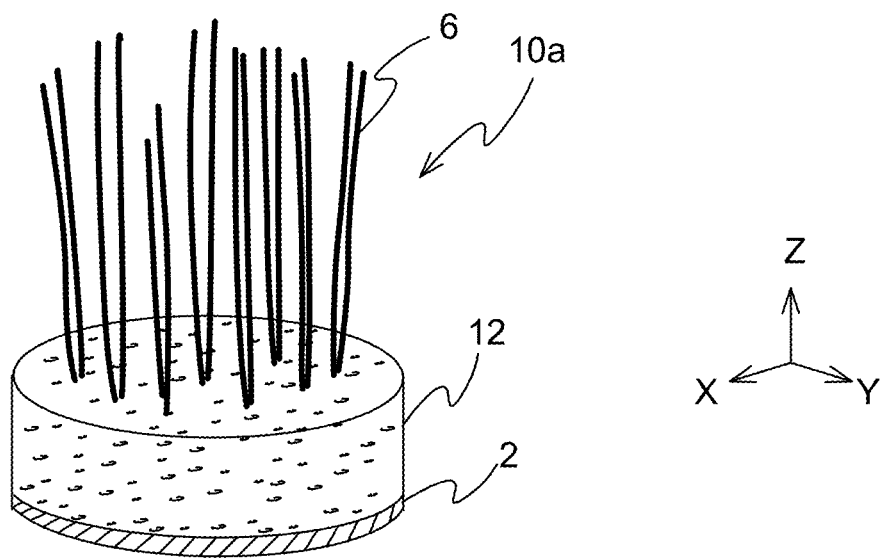
FIG. 12A) and FIG. 12(B) are schematic diagrams (No. 2) for explaining the manufacturing process of the sheet-like piece in FIG. 9.
Figure 12:
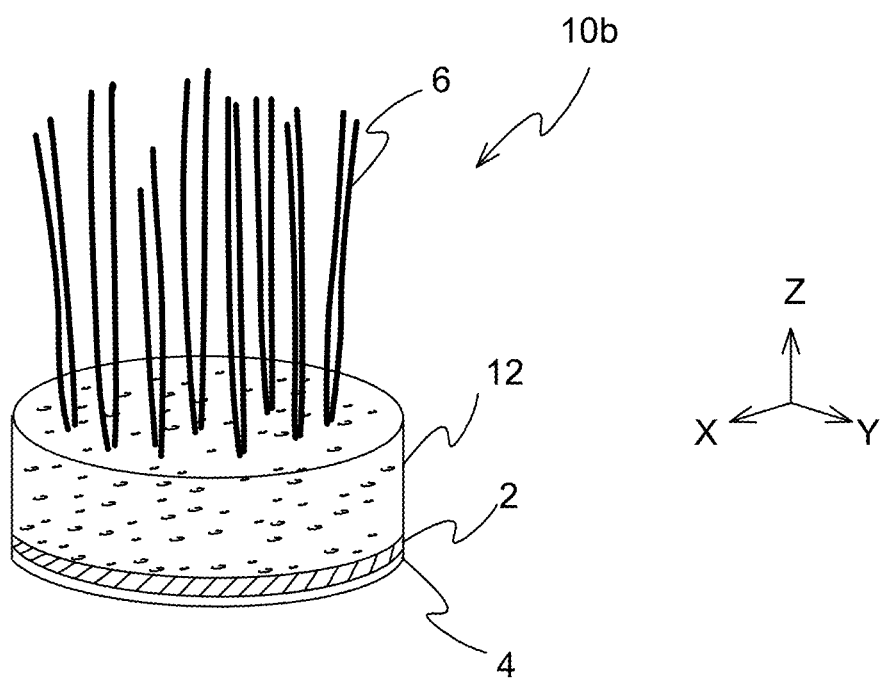

Next, the adhesion assisting layer 12 is adhered detachably on the +Z direction side surface of the base sheet 2 by using one adhesive agent to form the laminated body $1a$ shown in FIG. 11(B). Subsequently, the prostheses 6 is flocked at a predetermined density so as to penetrate the adhesion assisting layer 12 of the laminate body $1a$ and the base sheet 2 to produce the intermediate member $10a$ shown in FIG. 12(A).

Figure 13:
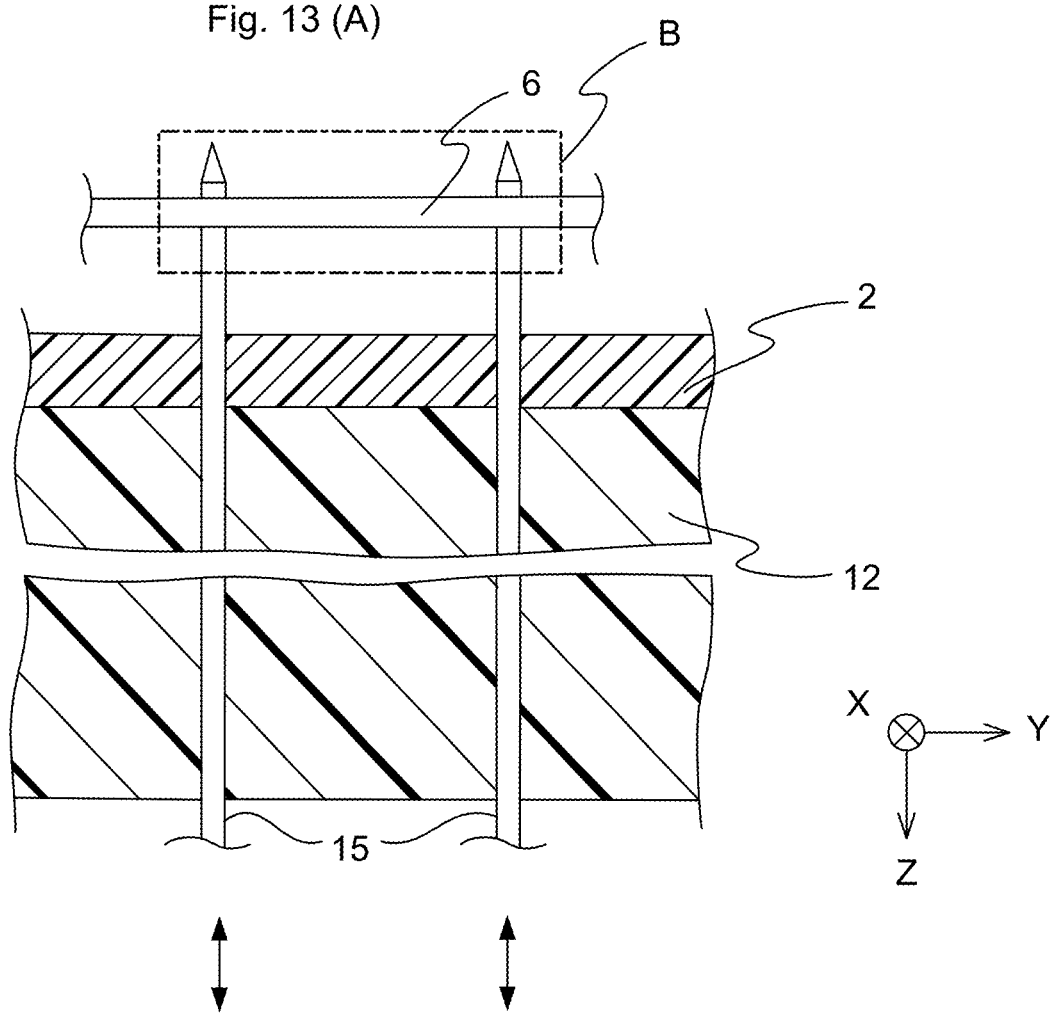
FIG. 13(A) and FIG. 13(B) show flocking the prostheses into the base sheet in Fig. 13(A), and an enlarged view Fig. 13(B) of B part in Fig 13(A). It is the figure for explaining the frocking the prostheses.
Figure 13:
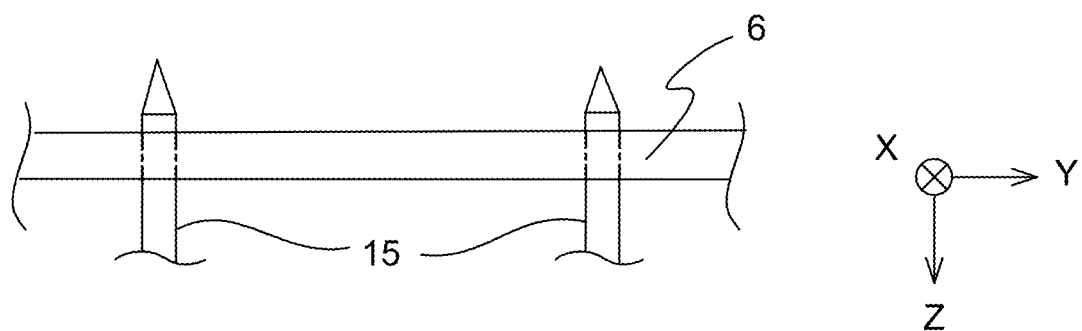

The flocking of the prostheses 6 into the laminate body 6 is performed by, for example, the V type flocking method. As shown in FIG. 13, on V type flocking, the prostheses 6 which is cut into a particular length is locked with a pair of guide needles 15, which is movable along with Z axis direction, at the −Z direction side of the base sheet 2. In that state, the guide needle 15 is moved to the +Z direction, while keeping the prostheses locked. As a result, the guide needle 15 moves to +Z direction and is pulled out while leaving the root portion $6a$ of the prostheses 6 on the −Z direction side of the base sheet 2. Thereafter, the UV curing adhesive agent is applied to the root portion $6a$ remained on −Z direction side of the base sheet 2, and the UV curing adhesive agent is cured by UV ray irradiation. Thus, the flocking of the prostheses 6 into the laminate body $1a$ is performed.

Returning to FIG. 12, when the intermediate member $10a$ is produced, the reservoir layer 4 is strongly adhered to the −Z direction side surface of the base sheet 2 by using the adhesive agent to produce the intermediate member $10b$ shown in FIG. $10b$. At this time, the reservoir layer 4 is preferably formed by depositing the layer upon layer having uniform thickness with the micro needle $4n$ so as to cover the entire back surface of the base sheet 2; because of the improving adhesiveness and saving natural appearance. Also, the layer preferably is about 1.5 to 2 times thicker than that of the base sheet 2, about 45 to 80 µm, because the tensile strength of the sheet for hair growth promotion of the invention is maintained to stably keep the prostheses 6 (it is sometimes referred to as "flocking material").

Subsequently, the pressure sensitive adhesive is applied on an area without the micro needle $4n$ in the −Z direction surface of the reservoir layer 4 of the intermediate member $10b$ so as to form mesh-shape for generating the adhesion layer 5, by this to produce the intermediate member $10c$ as shown in FIG. 14(A).

Next, the intermediate member $10c$ is cut in a desired size, and then the −Z direction surface of the adhesion layer 5 on the member $10c$ is adhered to the supporting member H. As a result, the sheet for hair growth promotion 10 is produced as shown in FIG. 14 (B).

Thus produced sheet for hair growth promotion 10 is placed on a ring-shaped sheet holder, made of metal sheet member or plastic sheet member, having a desired thickness and size, and the product is completed.

Since the adhesion layer 5 has a lattice shape, the hair growth sheet 10 of the invention does not suppress the hair extending from the scalp more than necessary. As a result, rapid hair growth occurs.

Also, the whitening and wrinkle ameliorating agent of the present invention is prepared by omitting the step to flocking the hair prostheses 6 on the base sheet 2 from the entire process for preparing the sheet for hair growth promotion 10, and adjusting the amount of the physiologically active substance used. The prepared whitening and wrinkle ameliorating agent may be cut to a variety of sizes depending on the application as shown FIGS. 18 (A) to 18 (D), and may be completed by placing on the supporting member H as the same as the sheet-like piece 1.

EXAMPLE

Example 1

(Production of the Immortalized SHED and Culturing Method Thereof)
(1) Agents for Extraction, Plasmid and the Like
(1-1) Reagent and Others for Plasmid Extraction Kanamycin (Kan), ampicillin (Amp), LB liquid medium and LB agar medium, glycogen, agarose, sterilized water, ammonium acetate, sodium acetate, sodium dodecyl sulfate and RNase A were used. Both 50 mg/mL kanamycin (Kan) and ampicillin (Amp) solutions were prepared to be stored as stock solutions at −20° C. Glycogen was prepared at the concentration of 20 mg/ml. 10 mg/ml RNase A was prepared to store at −20° C. 10 M (saturated) ammonium acetate ($NH_4OAc$) and 3 M sodium acetate (NaOAc; pH 5.2) were prepared.
(1-2) Restriction Enzyme and the Like

*E. coli* competent cell (Supercharge EZ10 Electro competent Cells, product code 636756), Swa I (the product code 1111A, Smi I is a comparable one), Xho I (the product code 1094A), T4 DNA Ligase (the product code 2011A), NucleoBond Xtra Midi (the product code 740410.10/.50/.100), NucleoSpin Plasmid (the product code 740588 10/50/250) were purchased from Takara Bio Inc. Pac I was purchased from New England Biolabs.
(1-3) Buffer and the Like 1×TE Buffer (10 mM Tris-HCl (pH 8.0) including 1 mM EDTA), and phenol:chloroform:isoamyl alcohol (25:24:1) were respectively prepared, wherein phenol was saturated with 100 mM Tris-HCl (pH 8.0). Ethanol was used either 100% or 70%. In order to purify pAdeno-X plasmid DNA used in a mini scale recombination, the following solutions 1 to 4 were prepared.

Buffer 1: 25 mM Tris-HCl including 10 mM EDTA and 50 mM glucose (pH 8.0) (after autoclave, stored at 4° C.)

Buffer 2: 0.2 M NaOH containing 1 SDS (prepared immediately before the time of use, tightly sealed and stored at room temperature)

Buffer 3: 5 M KOAc (after autoclave, stored at 4° C.)
Buffer 4: 10 mM Tris-HCl (pH 8.0) including 1 mM EDTA and 20 µg/ml of RNase (immediately before use, RNase is added, stored at −20° C.)
(2) Purification of Adenovirus and Reagents for β-Gal Assay HEK293 cell (ATCC #CRL1573) transformed by human type V adenovirus was used. HEK293 cell was cultured in a complete medium. The composition of the complete medium was DMEM (Dulbecco's Modified Eagle's Medium, the basal medium) supplemented with 100 unit/ml sodium penicillin G, 100 µg/ml streptomycin, 4 mM glutamine, and 10% FBS. Sodium penicillin G solution was prepared in 10,000 U/ml, streptomycin sulfate solution was prepared in 10,000 µg/ml, and they were stored as the stock solutions. In the culture, 60 mm plates, 100 mm plates, 6-well plate, T75 and T175 flasks were used.

Trypsin-EDTA (the product code CC-5012) was purchased from Takara Bio Inc. Phosphate buffered saline (PBS, without $Ca^{2+}$ and $Mg^{2\pm}$) and Dulbecco's phosphate buffered saline (DPBS, with $Ca^{2+}$ and $Mg^{2\pm}$) were prepared. Also, 0.33% neutral red stain solution, and 0.4% trypan blue stain solution were used. In β-gal assay, X-Gal (5-bromo-4-chloro-3-indolyl-β-D-galactopyranoside (25 mg/ml)) in dimethylformamide (DMF) solution was stored at −20° C. in a light resistant container. Luminescent β-gal Detection Kit II (the product code 631712, Takara Bio Inc.) was used.
(3) Preliminary Test
(3-1) Construction of Recombinant Adenovirus Including lacZ (pAdeno-X-lacZ)

HEK293 cells removed DMSO after thawing was resuspended in 10 mL of the complete medium. Then whole amount was transferred onto the culture plate having a diameter of 100 mm. After HEK293 cells adhered to the plate, the culture medium was removed. Then, the cells were washed once with sterile PBS. After that, 1 ml trypsin-EDTA was added to treat them for about 2 minutes. Next, 10 ml of the complete medium was added to stop the reaction of trypsin, and then the cells were mildly suspended. By using viable count, $10^5$ cells were transferred into the plate having 100 mm diameter including 10 mL medium to spread out evenly.

pShuttle2-lacZ (a positive control vector included in Adeno-X Expression System 1) and Adeno-X Viral DNA (PI-Sce I and I-Ceu I digested) included in the kit are used. According to a protocol attached in the kit, the recombinant adenovirus including lacZ was structured. It was infected to the target cells, SHED, and the expression of β-garactosidase was assayed to confirm the vector construction.
(3-2) Construction of the Recombinant pShuttle2 Plasmid Prior to the construction of the recombinant pShuttle2 Vector (herein below, it is referred to as "rpShuttle 2 Vector".), *E. coli* DH5a was transformed with pShuttle2 Vector and pShuttle2-lacZ Vector included in the kit. Transformants were selected on LB agar plate including 50 µg/ml kanamycin (herein below, it is referred to as "LB/Kan".). Bacterial cells obtained from a single colony were streaked on new LB/Kan to be incubated at 37° C. for overnight.

Next, hTERT, bmi-1, HPV-E6, and HPV-E7 were cloned into pShuttle2 by the following procedure. pShuttle2 vector was cleaved by using a restriction enzyme suitable for these genes. Next, referring pShuttle2 Vector Information Packet (PT3416-5) attached to the kit, multi cloning site matching DNA to be inserted was decided. The plasmid treated with the restriction enzyme was treated by using alkaline phosphatase to be purified.

According to the conventional method, target DNA fragments were prepared to be purified. The vector digested with the restriction enzyme and the gene fragments were ligated. By using the ligation product, DH5α cells (competent cell) were transformed. A portion of the competent cell was taken to be transformed by using a control vector, pShuttle2-lacZ Vector included in the kit to use as a positive control.

The mixture including transformed *E. coli* was plated on the LB/Kan agar plate to select kanamycin resistant (Kanr) transformant (a colony). Five to 10 Kan resistant clones were selected, and they were plated in a small amount of the liquid medium to be amplified. After confirmation that these clones have rpShuttle2 Vector, they were incubated overnight. Then, by using a commercially available silica gel adsorption column, the constructed plasmid DNA was purified according to the conventional method.

The plasmid DNA was treated with the restriction enzyme to be subjected to 1 agarose gel electrophoresis. Then, target recombinant plasmid was identified. By sequencing, the direction of the inserted fragment and inserted site were confirmed to identify the positive clone. The recombinant pShuttle2 plasmid DNA (herein below, it is referred to as "rpShuttle2 plasmid DNA") was directly transfected into the target cell, and then it was subjected to western blot to check the target protein preliminary.

(3-3) Double Digestion of rpShuttle2 Plasmid DNA with PI-Sce I/I-Ceu I

From the rpShuttle2 plasmid DNA produced as mentioned above, an expression cassette of the inserted gene was taken out by using PI-Sce I and I-Ceu I. According to in vitro ligation method written in the protocol attached to the kit, the expression cassette which was taken out was integrated into Adeno-X Viral DNA. 30 μL PI-Sce I/I-Ceu I double-digestion solution of the rpShuttle2 plasmid DNA was prepared. It was mixed with the reagents shown in the following table 1 entered into 1.5 ml of the sterilized micro centrifuge tube.

TABLE 1

| | Liquid measure (μL) | |
|---|---|---|
| Reagent and others | Tune 1 | Tube 2 (lacZ control) |
| sterilized water | 19.5 | 19.5 |
| 10 × double-digention solution | 3.0 | 3.0 |
| rpShuttle2 plasmid DNA (500 ng/μL) | 2.0 | — |
| pShuttle2-lac Z plasmid (500 ng/μL) | — | 2.0 |
| PI-Sce I (1 unit/μL) | 2.0 | 2.0 |
| I-Ceu I (5 unit/μL) | 0.5 | 0.5 |
| 10 × BSA | 3.0 | 3.0 |
| Total | 30.0 | 30.0 |

Next, after fully mixing, the micro centrifuge tube was lightly centrifuged, and then incubated for 3 hours at 37° C. The double digested reaction mixture (5 μL) was subjected to 1 agarose/EtBr gel electrophoresis together with 1 kb ladder (DNA size marker).

(3-4) Extraction by Using Phenol:Chloroform:Isoamyl Alcohol

The remains of the double-digestion solution (25 μL), 70 μL 1×TE Buffer (pH 8.0) and 100 μL PCI mixture were added into the centrifuge tube, the tube was mixed by using vortex. Then, the tube was centrifuged by using a micro centrifuge at 4° C. with 14,000 rpm for 5 minutes. Then, the aqueous layer was transferred to 1.5 ml of clean centrifuge tube. Here, 400 μL 95% ethanol, 25 μL 10 M ammonium acetate, and 1 μL glycogen (20 mg/ml) were added, and then mixed by using the vortex.

Next, it was centrifuged at 4° C. with 14,000 rpm for 5 minutes. Then, the supernatant was deleted by aspiration to obtain a pellet. 300 μL of 70% ethanol was added on the pellet, it was centrifuged for 2 minutes with 14,000 rpm. The supernatant was carefully aspirated to remove, the pellet was air dried about for 15 minutes.

After the pellet was dried, it was dissolved in 10 μL sterilized 1×TE Buffer (pH 8.0), and the solution was stored at −20° C. by time of use.

(4) Construction of the Recombinant Adeno-X Plasmid DNA (4-1) Subcloning of the Expression Cassette into Adeno-X Virus Genome The reagents shown in the following table 2 were sequentially added into the 1.5 ml of the sterilized micro centrifuge tube. Then, it was mildly mixed and lightly centrifuged. After that, it was incubated at 16° C. for overnight.

TABLE 2

| Reagent and others | Liquid measure (μL) |
|---|---|
| PI-Sce I/I-Ceu I digested pShuttle2 plasmid DNA | 2.0 |
| PI-Sce I/I-Ceu I digested pShuttle2-lac Z plasmid DNA | — |
| sterilized water | 3.0 |
| 10 × DNA Ligation Buffer | 1.0 |
| Adeno-X Viral DNA (250 ng/μL) | 3.0 |
| DNA Ligase (1 unit/μL) | 1.0 |
| Total | 10.0 |

90 μL of 1×TE Buffer (pH 8.0) and 100 μL of PCI mixture were added to each sample, and then it was mildly mixed by using vortex. It was centrifuged at 4° C. with 14,000 rpm for 5 minutes, and the aqueous layer was transferred to 1.5 mL of clean micro tube. Then, 400 μL of 95% ethanol, 25 μL of 10 M ammonium acetate solution, and 1 μL of glycogen (20 mg/ml) were added to the tube, and then it was mildly mixed by using the vortex.

It was subjected to the centrifugation at 4° C. for 5 minutes with 14,000 rpm, and the supernatant was removed by the aspiration to obtain the pellet. The following ethanol precipitation operation was the same as those of (3-4). After pellet was dried, it was dissolved in 15 μL of the sterile deionized water.

(4-2) Swa I Digestion of the Recombinant Adeno-X Plasmid DNA

The digestion solution as shown in the following table 3 was prepared, and added into each sample in the centrifuge tube. Then, they were incubated for 2 hours at 25° C.

TABLE 3

| Reagent and others | liquid measure (μL) |
|---|---|
| ligation product | 15 |
| 10 × Swa I Digestion Buffer | 2.0 |
| 10 × BSA | 2.0 |
| Swa I (10 units/μL) | 1.0 |
| Total | 20.0 |

80 μL at of 1×TE Buffer (pH 8.0) and 100 μL of PCI mixture were added to each sample, and then it was mildly mixed by using the vortex. It was centrifuged at 4° C. with 14,000 rpm for 5 minutes. The following ethanol precipitation operation was the same as those of (3-4), and the dissolved solution of the pellet was stored at −20° C. until use.

(4-3) Confirmation of the E. coli Transformant by the Recombinant Adeno-X Plasmid DNA The competent cell (E. coli) for the electroporation was transformed with the Swa I digested products obtained in (4-2) by using Supercharge EZ10 Electrocompetent Cell (the product code 636756).

The transformant mixture was plated on the agar plate, which is the mixture of LB medium and ampicillin (final concentration 100 μg/mL) (herein below, it is referred to as "LB/Amp agar plate".), and then they are incubated at 37° C. for overnight. About $10^6$ of colonies were obtained as ampicillin resistant (Ampr) transformant. The obtained colonies were checked by using Adeno-X System PCR Screening Primer Set attached to the product.

The bacterial cells from the single colony were plated in 5 mL of fresh LB/Amp liquid medium, and incubated overnight. The next day, according to the mini-scale method as mentioned below, Adeno-X plasmid DNA was purified.

(4-4) Mini-Scale Preparation of the Recombinant Adeno-X Plasmid DNA 5 mL of log-phase medium was centrifuged with 14,000 rpm for 30 seconds to remove the supernatant. The pellet was centrifuged at 10,000 rpm for 1 minute again, and then the supernatant was removed by using the micropipette. 150 µL of the buffer 1 was added to it and mildly pipetted to resuspend. 150 µL of the buffer 2 was added to the cell suspension. Then the cell suspension were mildly inverted and stood for 5 minutes on ice. 150 µL of the buffer 3 was added to the cooled cell suspension, and then it was inverted again and stood for 5 minutes on ice.

The cell suspension was centrifuged at 4° C. with 14,000 rpm for 5 minutes, and the clear supernatant was transferred into 1.5 ml of the centrifuge tube. 450 µL of PCI mixture was added to the supernatant, and then inverted to mix. Then, it was centrifuged at 4° C. with 14,000 rpm for 5 minutes, and the aqueous layer was transferred to clean 1.5 ml of the micro centrifuge tube.

The following ethanol precipitation operation was the same as those of (4-1), and the dissolved solution of the pellet was stored at −20° C. until use. The target rDNA was identified by using the analysis with the restriction enzyme and PCR as described below.

(5) Analysis of Restriction Site of the Obtained rAdeno-X Plasmid DNA

Analysis was performed by using PI-Sce I and I-Ceu I. The reagents shown in the following table 4 was entered into 1.5 ml of the micro centrifuge tube. Then, 30 µL of PI-Sce I/I-Ceu I double digestion solution was added to it, and then fully mixed and then they were lightly rotated to collect the contents.

TABLE 4

| Reagent and others | liquid measure (µL) |
| --- | --- |
| sterilized water | 19.5 |
| 10 × double-digestion solution | 3.0 |
| rpAdeno-X DNA (500 ng/µL)(500 ng/µL) | 2.0 |
| pShuttle2-lac Z plasmid (500 ng/µL) | — |
| PI-Sce I (1 unit/µL) | 2.0 |
| I-Ceu I (5 unit/µL) | 0.5 |
| 10 × BSA | 3.0 |
| total | 30.0 |

It was incubated at 37° C. for 3 hours to perform restriction treatment. The treated mixture was subjected to 1% agarose/EtBr gel electrophoresis.

(6) Production of the Recombinant Adenovirus (6-1) Preparation of the rAdeno-X Plasmid DNA for Transfection of HEK293 Cells The reagents shown in the following table 5 were entered into the 1.5 ml of sterilized centrifuge tube to be mixed, and then it was lightly centrifuged by using the micro centrifuge. Then, it was incubated at 37° C. for 2 hours to treat the rAdeno-X plasmid DNA with Pac I restriction enzyme.

TABLE 5

| Reagent and others | liquid measure (µL) |
| --- | --- |
| sterilized water | 20 |
| pAdeno-X plasmid DNA (500 ng/µL) | 10 |
| 10 × Pac I Digestion Buffer | 4 |
| 10 × BSA | 4 |
| Pac I (10 units/µL) | 2 |
| total | 40 |

60 µL of 1×TE Buffer (pH 8.0) and 100 µL of PCI mixture were added to it, and then they were mildly mixed by using the vortex. Then, it was centrifuged by using the micro centrifuge at 4° C. for 5 minutes with 14,000 rpm. The aqueous layer was carefully transferred into 1.5 ml of the clean sterilized centrifuge tube.

The following ethanol precipitation operation was the same as those of (3-4), and the dissolved solution of the pellet was stored at −20° C. until use.

(6-2) Transfection of Pac I Digested Adeno-X Plasmid DNA into HEK293 Cell

Before 24 hours of the plasmid DNA transaction, HEK 293 cells were plated on the 60 mm culture plate so as that the cell number was 1 to 2×10$^6$ (about 100 cells/mm$^2$). Then, they were incubated at 37° C. under the presence of 5% $CO_2$.

10 µL of Pac I-digested Adeno-X plasmid DNA was transfected to each culture plate to introduce Adeno-X DNA into the HEK293 cell, according to a standard transfection method (CalPhos Mammalian Transfection Kit, the product code 631312, Takara Bio Inc.). Occurrence of CPE (cytopathic effect) was confirmed from the next day of the transfection.

One week later, the cells adsorbed on the bottom or side wall was released by mild mixing. The obtained cell suspension was transferred into 15 mL of the sterilized centrifuge tube having a conical bottom, and it was centrifuged at room temperature for 5 minutes with 1,500×g.

Obtained precipitate was suspended in 500 µL of the sterilized PBS. The solution was subjected to the free-thaw operation in three times, which is frozen in dry ice/ethanol and thawed in the incubator with 37° C., to obtain the lysate in which the cells were fully thawed. Next, it was lightly centrifuges to remove suspended matter, and then transferred into the sterilized another tube to use immediately. The lysate did not use immediately was stored at −20° C. 250 µL of the lysate was added onto the cultured cells in the plate with 60 mm diameter, and continued to incubate. Note that by using anti-Hexon antibody included in Adeno-X Rapid Titer Kit (the product code 631028, Takara Bio Inc.), the adenovirus was titrated according to the instruction manual (PT3651-1) of the kit.

(6-3) Virus Amplification for Preparing the Virus Having High Titer

Prior to 24 hours of the titration, HEK293 cells were plated on T75 flask, and incubated at 37° C. in the presence of 5% $CO_2$ for overnight to confirm that they became 50 to 70% of confluent.

In the next day, the medium including the virus was exchanged, and infected by the virus at MOI=10. After the incubation at 37° C. in the presence of 5% $CO_2$ for 90 minutes, the flask was taken out and 10 mL of the medium was added into the flask.

They were cultured at 37° C. for 3 to 4 days in the presence of 5% $CO_2$, and CPE was confirmed. After released 50% of the cells, the released cell suspension was prepared as described above; it was transferred to 15 mL of the sterilized centrifuged tube with the conical bottom. The freeze and thaw operation as described above was performed and the cells were thawed. By using Adeno-X Rapid Titer Kit (the product code 631028), the titer, 10$^7$ PFU/mL was obtained. It was subjected to Western blotting, it was confirmed whether the packaged adenovirus genome has copies of the specific transcription unit against the target gene as the functional form.

(7) Adenovirus Infection to the Target Cells
(7-1) Infection to the Target Cells 24 hour before the infection, 1×10⁶ cells of SHED were plated on 6-well plate. In the next day of the plating, the medium was removed, and 1.0 mL of the medium including virus was added to the center of each plate. The solution was evenly spread on a monolayer formed by the SHED.

It was incubated at 37° C. for 4 hours under 5% $CO_2$, and the virus was infected to SHED. Next, the fresh medium was added, and then incubated at 37° C. in under 5% $CO_2$. 24 to 48 hours after the infection, the expression of the introduced gene was analyzed time dependently.

(7-2) Analysis of the β-Galactosidase Expression of the Infected Cells

The β-galactosidase expression in the adherent cell infected with the Adeno-X-lacZ was assayed by using Luminescent β-gal Detection Kit II (the product code 631712, Clontec Laboratories Inc.).

Example 2

(1) Production of SHED

The exfoliated deciduous teeth from 10 years old healthy boy were used. After the exfoliated deciduous teeth was disinfected with Isodine solution, a crown of the teeth was horizontally cut by using the dental diamond point, and then the dental pulp tissue was collected by using the dental reamer. The obtained dental pulp tissue was digested in the solution of 3 mg/mL of type I collagenase and 4 mg/mL of disperse at 37° C. for 1 hour. Next, the solution was filtrated by using 70 mm of cell strainer (Falcon).

The filtrated cells were resuspended in 4 mL of the medium, and the culture dish having the 60 mm of diameter to be plated. DMEM (Dulbecco's Modified Eagle's Medium) including 10% FCS was added into the dish and cultured at 37° C. for about 2 weeks in the incubator prepared under 5% $CO_2$ at 37° C. The adherent cells formed colonies (the dental stem pulp cells) were treated by using 0.05% trypsin-0.2 mM EDTA for 5 minutes at 37° C., and then the cells released from the dish were collected.

Next, the adherent cells selected as mentioned above were plated on the culture dish for the adherent cells (a collagen coat dish), and they were incubated in the incubator prepared under 5% $CO_2$ at 37° C. as the primary culture to obtain the primary cultured cell. When the cells became macroscopically sub-confluent (in the case, about 70% of the surface of the culture container was covered by the cells), or confluent, the cells were treated by using 0.05% trypsin-0.2 mM EDTA at 37° C. for 5 minutes to release the cells from the container, and then collected. Thus obtained cells were again plated on the dish including the medium, and several passages were performed until the cell number became about 1×10⁷ cells/mL. Obtained cells were stored in liquid nitrogen.

After that, by using the primary cultured cells, the passage was performed at the cell concentration in about 1×10⁴ cells/cm². In the experiment, the cells passed from 1 to 3 were used. The human BMMSC (the bone marrow mesenchymal stem cell, Bone Marrow Mesenchymal stem cells) was purchased from Lonza Group Ltd. and cultured according to the instruction manual provided from the manufacturer. As described above, human exfoliated deciduous teeth dental pulp stem cell (SHED) was obtained. Among the obtained SHED, about 1×10⁶ cells of STRO-1 expression cells were sorted from each sample by using FACSTAR-PLUS (Becton, Dickinson and Company) as follows:

According to the manufacturer's instruction manual of the bromodeoxyuridine BrdU staining kit (Invitrogen), BrdU was incorporated during 12 hours to evaluate the growth speed of SHED (n=3 in each group). The experiments were repeated 5 times. After one-way analysis of variance, Tukey-Kramer test was performed to evaluate statistical significant difference.

In order to detect STRO-1 with immunofluorescence, SHED was fixed by using 3% paraformaldehyde, and rinsed twice with PBS and then treated by using 100 mM of glycine for 20 minutes. Next, these cells were permeabilized with 0.2% of Triton-X (Sigma-Aldrich) for 30 minutes. Then, it was incubated in the mixture of 5% donkey serum and 0.5% of bovine serum albumin for 20 minutes.

Next, The cells were incubated with the primary antibody, mouse anti-human STRO-1 antibody (1:100, R&D Inc.) for 1 hour, then incubated with the secondary antibody, goat anti-mouse immunoglobulin M-FITC antibody (1:500, Southern Biotech Corp.) for 30 minutes, and then mounted by using Vector Shield DAPI (Vector Laboratories Inc.). After that, α-MEM supplemented with 15% of FBS was added to the 6-well plate, and then the sorted cells were plated in each well for preparing clones. About 300 colonies among the grown cells were pooled for the test.

(2) Transgenesis

As described above, 4 genes, bmi-1, E6, E7 and hTERT were integrated into the adenovirus vector to create a virus vector to express the gene products. As a reference, the control vector to which these genes were not integrated was created.

SHED was plated on the collagen coat dish having 100 mm of the diameter at the concentration of 1×10⁶ cells, and then DMEM supplemented with 10% FBS was added. They were cultured until sub-confluent. The medium was removed by aspiration, and 500 µL of the virus solution diluted with the medium was added (MOI=10) at 37° C. for 1 hour in the 5% $CO_2$ incubator to infect the virus vector. After 48 hours from the infection, the infected cells were incubated for 10 days in the medium supplemented with puromycin (1 pg/mL) to select the resistant clone. Then, the 500 to 600 of resistant clones were pooled. Every 3 to 4 days, about 0.5×10⁵ cells of SHED were plated to the culture dish having 100 mm of the diameter to perform passage. SHED to which the genes were transferred was named SHED-T, and that to which the genes were not transferred was named SHED-C.

Example 3

(1) Measurement of the Growth Rates of SHED-C and SHED-T

Status of the population doubling time of SHED-T (the gene transferred SHED) was shown in FIG. 5. In the figure, a vertical axis shows the population doubling time number (cell division number, times), and an abscissa axis shows the period (date of culture). Evaluation standard for the aging was the status wherein SHED in culture does not divide for 1 month. The growth of SHED-C has stopped about 30 times to enter aging or growth termination phase. In contrast, SHED-T passed over 250 PD and grown after 800 days has passed.

(2) Flow Cytometry Analysis

In order to obtain a single cell suspension, the adherent monolayer cells were digested with trypsin/EDTA. The anti-STRO-1 monoclonal antibody (1:100) was added to 2×10⁵ cells and stood to analyze by using FACS Calibur flow cytometer (Becton, Dickinson and company). Compared to the control antibody with corresponding to the same isotype, the expression was positive when the fluorescence level of them was higher more than 99% in the ratio. In both of SHED-T and SHED-C, the primary and later passage cells were fixed, and stained with FITC binding STRO-1 antibody. Then, it was analyzed by using the flow cytometry. The test was repeated twice. In SHED-C, the ratio of the STRO-1 positive cells was 27% at PD20, and decreased 15% at PD30 (FIGS. 8(A) and (B)). The ratio of the STRO-1 positive cells in SHED-T was 46% at PD20 and 41% at PD40, respectively (FIGS. 6 (C) and (D)).

(3) Study for the Proliferation

The proliferation abilities of SHED-C or SHED-T at PD0, PD10 and PD20 were studied by using the forming ability of the new bone mass and histological stain. Firstly, $2.0 \times 10^6$ cells of SHED-C or SHED-T were mixed with 40 mg of ceramic powder of hydroxyapatite/tricalcium phosphate (HA/TCP) (Plympus Corporation), and then the mixture was inoculated subcutaneously under a dorsal surface of immunodeficiency mouse at 10 weeks age (NIH-bgnu-xid, female, Harlan Sprague Dawley Inc.).

Eight weeks after the inoculation, the inoculant was recovered, and fixed by using 4% formalin to decalcify. Then, it was buffered by using PBS solution including 10% EDTA for paraffin embedding. A part of it was stored in 70% ethanol for embedding in resin.

A paraffin section was deparaffinized, and hydrated. After that, the section was stained with hematoxylin and eosin (herein below, it is referred to as "H&E".). FIGS. 7 (A) to (C) show the stained images of SHED-T (the immortalized cell)) at PD0 to PD20, and the same Figs. (D) to (F) show the stained images of SHED-C (the normal cell) at PD0 to PD20. In order to determine the new born formation in vivo, the specified area was chosen, and the area of the new born and the sight area were calculated to obtain the new born mass from these values for the inoculant formed after SHED-T inoculation or SHED-C inoculation.

New born mass=New born area/sight area×100

FIG. 8 shows the change of the new born mass of SHED-T and SHED-C at the population doubling number (doubling time). In the figure,  shows $p<0.05$, * shows $p<0.01$. Note that the new born mass was obtained by using the following equation.

As shown in FIG. 8, the new bone mass was decreased depending on the increase of the population doubling time in SHED-C, and it was decreased to about ⅕ at PD20 compared to that of PD0. In contrast, the bone mass was not changed by PD20 in SHED-T, and the bone mass in SHED-T showed 5 times higher than that of SHED-C at PD20.

(4) Evaluation of Canceration Activity $1 \times 10^6$ cells of SHED-C cells or SHED-T cells were inoculated to the subcutaneous tissue of immunodeficiency mouse. After inoculation, we performed the observation more than 30 days. However, the tumor was not formed in the mice to which the cells were transplanted during the observation term. Also, all of the clones from the cultured cells did not show any morphological change between the ranges from 40 PD to 200PD in SHED-T cells.

By this, it was demonstrated that SHED-T had no canceration activity.

(5) Evaluation

It was demonstrated that SHED-T had growth ability, holding differentiation ability even after 260PD. However, SHED-C had the differentiation ability, but had aged less than 30 PD.

As described above, it was demonstrated that SHED-T became the immortalized stem cell, and is suitable for large scale production of SHED supernatant having higher activity.

Example 4

(1) Preparation of Sheet-Like Piece

About 0.2 to 4 wt % of dextran was mixed with hyaluronic acid in a glass container, and a desired amount of the lyophilized powder of the culture supernatant was added to be mixed with them to prepare a reservoir layer forming material.

Next, a resin sheet was formed with commercially available photosensitive resin to form micro needle pattern having a shape shown in FIG. 2(A) by using photolithography method. After that, the pattern was printed by electroforming processing to produce a mold for forming the micro needles. The mold was formed as a square about 10 cm on a side or rectangle of 7 cm×15 cm.

Also, the concave portion to form the micro needles was formed as in conical shape which has an upper diameter of about 0.2 mm, a bottom diameter of about 0.04 mm and a depth of about 0.8 mm, and arranged in a lattice pattern. The concave portion is about $75/cm^2$.

Water was added to the reservoir layer forming material to prepare an aqueous solution containing about 10% solid content. Then, it was poured into the mold at room temperature, and was evaporated to remove water to dry. After drying, the reservoir layer having the micro needles was obtained by peeling off the mold.

Subsequently, sheet-like piece was prepared in the same manner as shown in FIG. 3(C) to FIG. 4(B). That is, the adhesion assisting layer 12 was adhered to one side of the base sheet 2 by using an adhesive agent. The reservoir layer 4 was adhered on another surface of the base sheet 2 without adhesion assisting layer. Next, the mesh-patterned adhesion layer 5 was formed on the area without the micro needles 4*n* to produce a ultra-thin sheet. On the ultra-thin sheet, the supporting member H, urethane for fixing, was laid over to prepare the sheet-like piece with the structure as shown in FIG. 1.

The sheet-like piece of the present invention was cut to the sheet-shaped piece with desired size and shape as shown in FIG. 18 (A) to (D). After that, the sheet-shaped piece is placed on a sheet holder put on a plate member made of metal or plastic with the desired size and the desired thickness, and it was shielded with a light-shielding film to produce the complete product. These products were stored in a refrigerator until use. The sheet holder has a structure covering the periphery of the sheet-shaped piece with about 1 mm width to maintain the structure of the micro needle.

(2) Application of Sheet for Promoting Hair Growth

The sheet for promoting hair growth 1 produced as described above was produced by the procedure shown in FIG. 3 (A) to FIG. 4 (B).

The sheet for promoting hair growth 1 prepared as described above was applied onto the scalp of a male as shown in FIG. 15. After applying and appressing the sheet for promoting hair growth 1 there, the adhesion assisting layer was peeled off. In the example, in order to make it easier to see the applied state of the sheet of the present invention, the base sheet without flocking material was used. The resulting photo images with the digital camera are shown in FIG. 16(A) to (C).

Baldness of hair before the application are shown in 1 to 3 of FIG. 16 (A), those after the application from 3 to 7 days are shown in 1 to 3 of FIG. 16 (B) and also in 1 to 3 of FIG. 16 (C). As clearly shown in the baldness of the hair before and after the application of the sheet, hair growth was observed after 3 days of the application, and thereafter time-dependent increase of the hair growth amount was observed (see the inside the white circle in FIGS. 16 (B) 1 to 3). In particular, it was observed that plural strands of hair were grown at one site in the image after 7 days (see FIG. 16 (C) 3).

Figure 17:
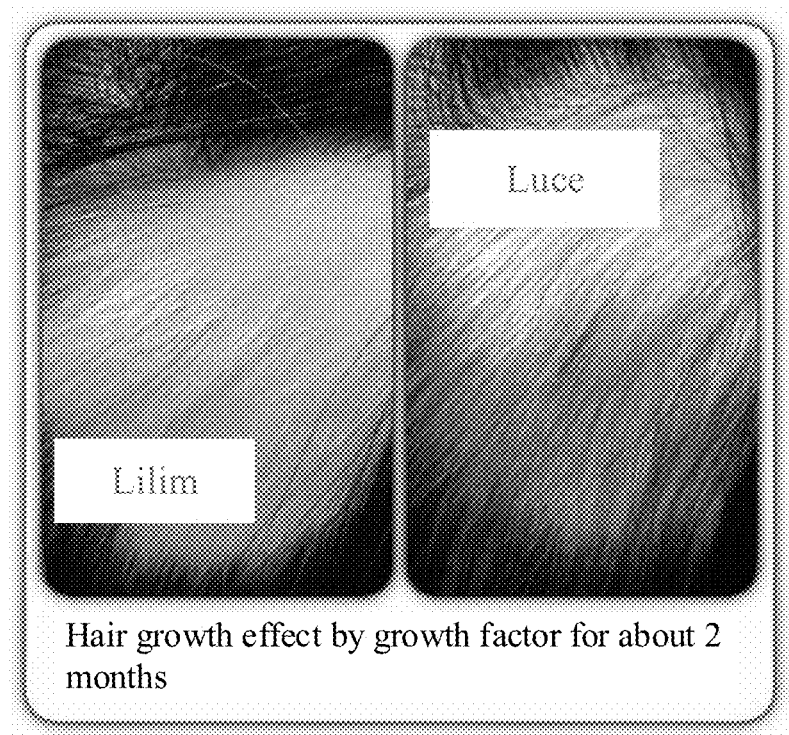
FIG. 17(A) and FIG. 17(B) are photographs showing the change of the area before and after applying the sheet for hair growth promotion of the invention to head.
Figure 17:

Also, a change in the area with gray hair, on which the sheet was applied, is shown in FIG. 17 (A). The left side image of (A) shows that before the start of application of the sheet of the present invention, and the right side image shows that after about 2 months from the application, during the 2 month, the 5 sheets were applied. Although in the area from which most of hair fell out, only gray strands of hair were remained before the application, it was confirmed the increase of the hair growth and newly grown black strands of hair.

A change in the area on which the sheet was applied is shown in FIG. 17 (B). The left side image of (B) shows before the start of application of the sheet of the present invention, and the right side image shows that after about 2 months from the application, during the 2 month, the 5 sheets were applied. Although in the area from which most of hair fell out, only gray strands of hair were slightly remained before the application, it was confirmed the increase of the hair growth and newly grown black strands of hair.

From the above, it was confirmed that normal growth of the hair was promoted in the area where the sheet for promoting hair growth of the invention was applied.

INDUSTRIAL APPLICABILITY

The present invention is useful to the beauty care field.

EXPLANATION OF REFERENCE NUMERALS

1, sheet-like piece
2, base sheet
4, reservoir layer
5, adhesion layer
6, hair prostheses (hair member)
6a, root part (implantation part)
6b, free end
8, fixed part
10, sheet for promoting hair growth
12, adhesion assisting layer
15, guide needle
H, supporting member

The invention claimed is:

1. A sheet-like piece comprising:
a base sheet made of an elastic material;
a reservoir layer, which contains a physiologically active substance, with plural micro needles extending in opposite direction to said base sheet, being arranged on one side surface of the base sheet ;
a mesh-formed adhesion layer formed on the opposite side surface of the reservoir layer adhered to the base sheet; and
an adhesion assisting layer being detachably arranged on the opposite surface, from which said reservoir layer is formed, of said base sheet,
wherein a tip of said micro needle protrudes from said adhesion layer;
wherein the plural micro needles are formed on the reservoir layer, and that concave portions for forming the micro needles have a conical shape which has upper diameter of about 0.1 to 0.3 mm, bottom diameter of about 0.03 to 0.05 mm and depth of about 0.6 to 1.0 mm; and
said adhesion assisting layer is composed of a spongy member.

2. The sheet-like piece according to the claim 1, wherein said elastic material is composed of a translucent synthetic resin having moisture permeability with less than 0.1 mm of thickness.

3. The sheet-like piece according to the claim 1, wherein said reservoir layer comprises a mixture of a water soluble polymer, and either a monosaccharide or a disaccharide, and a mixture of said physiologically active substance.

4. The sheet-like piece according to the claim 3, wherein said water soluble polymer is at least any one of the polymer selected from the group consisting of collagen, gelatin, hyaluronic acid, dextrin, dextran, proteoglycan, sodium chondroitin sulfate, carboxymethyl cellulose, hydroxyethyl cellulose hyaluronic acid and physiologically acceptable salt thereof.

5. The sheet-like piece according to the claim 3, wherein said monosaccharide or said disaccharide is any one selected from the group consisting of glucose, fructose, sucrose, lactose, trehalose and mixture at least two thereof.

6. The sheet-like piece according to the claim 1, wherein said adhesion layer is formed by silicon based adhesive agent for medical purposes.

7. The sheet-like piece according to the claim 1, wherein said spongy member is composed of any one of material selected from the group consisting of urethane, silicon, pulp paper, styrene, vinyl and cloth.

* * * * *